(12) United States Patent
Henley et al.

(10) Patent No.: US 6,933,417 B1
(45) Date of Patent: Aug. 23, 2005

(54) PROCESS FOR VINYL CHLORIDE MANUFACTURE FROM ETHANE AND ETHYLENE WITH PARTIAL CHL RECOVERY FROM REACTOR EFFLUENT

(75) Inventors: John P. Henley, Midland, MI (US); Mark E. Jones, Midland, MI (US); Daniel A. Hickman, Midland, MI (US); Kenric A. Marshall, Lake Jackson, TX (US); Daniel J. Reed, Angleton, TX (US); William D. Clarke, Brazoria, TX (US); Michael M. Olken, Midland, MI (US); Lee E. Walko, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 213 days.

(21) Appl. No.: 10/130,102

(22) PCT Filed: Oct. 6, 2000

(86) PCT No.: PCT/US00/27701

§ 371 (c)(1),
(2), (4) Date: May 14, 2002

(87) PCT Pub. No.: WO01/38274

PCT Pub. Date: May 31, 2001

Related U.S. Application Data
(60) Provisional application No. 60/166,897, filed on Nov. 22, 1999.

(30) Foreign Application Priority Data

Oct. 3, 2000 (WO) ................ PCT/US00/27272

(51) Int. Cl.[7] .................. C07C 17/15; C07C 17/152; C07C 17/158
(52) U.S. Cl. .................. 570/224; 423/481; 423/502; 423/493; 423/472; 423/500; 570/216; 570/219; 570/223
(58) Field of Search ................ 423/481, 502, 423/493, 472, 500; 570/216, 219, 223, 224

(56) References Cited

U.S. PATENT DOCUMENTS

| | | | |
|---|---|---|---|
| 2,204,733 A | 6/1940 | Miller | 23/219 |
| 3,488,398 A | 1/1970 | Harpring et al. | 260/659 |
| 3,629,354 A | 12/1971 | Beard et al. | 260/683.3 |
| 3,634,330 A | 1/1972 | Yerres et al. | 252/441 |
| 3,644,561 A | 2/1972 | Beard et al. | 260/683.3 |
| 3,657,367 A | 4/1972 | Blake et al. | 260/659 A |
| 3,658,933 A | 4/1972 | Beard et al. | 260/683.3 |
| 3,658,934 A | 4/1972 | Beard et al. | 260/683.3 |
| 3,702,311 A | 11/1972 | Beard et al. | 252/441 |
| 3,769,362 A | 10/1973 | Beard et al. | 260/677 XA |
| 3,927,131 A | 12/1975 | Ward | 260/654 D |
| 3,968,200 A | 7/1976 | Tsao | 423/488 |
| 4,042,640 A | 8/1977 | Tsao | 260/659 |
| 4,046,821 A | 9/1977 | Croce et al. | 260/654 A |
| 4,046,823 A | 9/1977 | Gordon et al. | 260/662 R |
| 4,100,211 A | 7/1978 | Magistro | 260/656 R |
| 4,110,251 A | 8/1978 | Lauder et al. | 252/442 |
| 4,230,668 A | 10/1980 | Sheely et al. | 422/140 |
| 4,300,005 A | 11/1981 | Li | 570/224 |
| 4,319,062 A | 3/1982 | Boozalis et al. | 570/220 |
| 4,323,482 A | 4/1982 | Stiles et al. | 252/462 |
| 4,329,525 A | 5/1982 | Riegel et al. | 570/191 |
| 4,375,569 A | 3/1983 | Kroenke et al. | 570/224 |
| 4,402,942 A | 9/1983 | Melin | 424/177 |
| 4,405,500 A | 9/1983 | Muller et al. | 252/433 |
| 4,460,699 A | 7/1984 | Convers et al. | 502/84 |
| 4,462,970 A | 7/1984 | Pastor et al. | 423/263 |
| 4,528,174 A | 7/1985 | Schmidhammer et al. | 423/488 |
| 4,529,410 A | 7/1985 | Khaladji et al. | 51/309 |
| 4,590,216 A | 5/1986 | Dombek | 518/700 |
| 4,727,201 A | 2/1988 | Cobb | 570/202 |
| 4,737,594 A | 4/1988 | Olah | 570/222 |
| 4,754,088 A | 6/1988 | Schmidhammer et al. | 570/247 |
| 4,766,103 A | 8/1988 | Cobb | 502/217 |
| 4,783,564 A | 11/1988 | Piotrowski et al. | 570/254 |

(Continued)

FOREIGN PATENT DOCUMENTS

| | | | |
|---|---|---|---|
| EP | 0162 457 B1 | 7/1989 | C07C/17/34 |
| EP | 0 372 183 B1 | 1/1997 | C07C/11/107 |
| EP | 0 667 845 B1 | 1/1998 | C07C/17/154 |
| FR | 1 594 693 | 7/1970 | |
| GB | 1 039 369 | 8/1966 | |
| GB | 1 040 962 | 9/1966 | |
| GB | 1 141 369 | 1/1969 | C07C/19/02 |
| GB | 1 213 202 | 11/1970 | C07C/21/06 |
| GB | 1373296 | 11/1974 | C07C/17/10 |
| GB | 1 475 358 | 6/1977 | C07C/17/15 |
| GB | 1 492 945 | 11/1977 | |
| GB | 2 095 242 | 9/1982 | |
| GB | 2 101 596 A | 1/1993 | |
| WO | WO 01/38271 | 5/2001 | |
| WO | WO 01/38272 | 5/2001 | |
| WO | WO 01/38273 | 5/2001 | |
| WO | WO 01/38274 | 5/2001 | |
| WO | WO 01/38275 | 5/2001 | |
| WO | WO 01/42176 | 6/2001 | |

OTHER PUBLICATIONS

Wm. C. Conner, Jr. et al., The Oxyhydrochlorination of Methane on Fumed Silica–Based Cu, K, La Catalysts: III Bulk & Surface Analysis, Applied Catalysis, vol. 11, pp. 59–71, 1984.

(Continued)

*Primary Examiner*—Johann Richter
*Assistant Examiner*—Elvis O. Price

(57) ABSTRACT

A process for producing vinyl chloride monomer from ethylene and ethane having input of significant quantities of both ethane and ethylene in input streams to the affiliated reactor where hydrogen chloride in the reactor effluent is only partially recovered from the reactor effluent in the first unit operation after the ethane/ethylene-to-vinyl reaction step or stage. Steps are presented of oxydehydrochlorination catalytic reaction of ethane, ethylene, hydrogen chloride, oxygen, and chlorine; cooling and condensing the reactor effluent stream; and separating the condensed raw product stream into vinyl chloride monomer and a reactor recycle stream.

44 Claims, 3 Drawing Sheets

U.S. PATENT DOCUMENTS

| | | | |
|---|---|---|---|
| 4,849,562 A | 7/1989 | Buhs et al. | 570/241 |
| 4,859,432 A | 8/1989 | David et al. | 423/21.1 |
| 4,899,000 A | 2/1990 | Stauffer | 570/222 |
| 4,942,697 A | 7/1990 | Khaladji et al. | 51/283 R |
| 4,965,057 A | 10/1990 | David et al. | 423/263 |
| 5,008,225 A | 4/1991 | Magistro | 502/73 |
| 5,013,534 A | 5/1991 | Dissaux et al. | 423/263 |
| 5,023,070 A | 6/1991 | Le Loarer | 423/592 |
| 5,061,670 A | 10/1991 | Forquy et al. | 585/500 |
| 5,072,063 A | 12/1991 | Langensee | 570/236 |
| 5,087,791 A | 2/1992 | Magistro | 585/657 |
| 5,097,083 A | 3/1992 | Stauffer | 570/241 |
| 5,099,085 A | 3/1992 | Strasser et al. | 570/245 |
| 5,113,027 A | 5/1992 | Mainz et al. | 570/224 |
| 5,114,702 A | 5/1992 | Pederson et al. | 423/639 |
| 5,137,862 A | 8/1992 | Mackrodt et al. | 502/303 |
| 5,178,664 A | 1/1993 | Picard | 75/300 |
| 5,179,215 A | 1/1993 | Ramachandran et al. | 549/262 |
| 5,210,358 A | 5/1993 | Magistro | 585/500 |
| 5,227,549 A | 7/1993 | Correia et al. | 570/243 |
| 5,232,889 A | 8/1993 | Blanchard et al. | 502/263 |
| 5,262,547 A | 11/1993 | Ramachandran et al. | 549/262 |
| 5,352,646 A | 10/1994 | Blanchard et al. | 502/263 |
| 5,397,758 A | 3/1995 | Bouruetaubertot et al. | 502/303 |
| 5,453,557 A | 9/1995 | Harley et al. | 585/641 |
| 5,466,837 A | 11/1995 | Ramachandran et al. | 549/262 |
| 5,492,878 A | 2/1996 | Fujii et al. | 502/304 |
| 5,496,528 A | 3/1996 | David et al. | 423/263 |
| 5,510,546 A | 4/1996 | Ito | 570/236 |
| 5,580,536 A | 12/1996 | Yao et al. | 423/263 |
| 5,599,588 A | 2/1997 | Poncelet | 427/343 |
| 5,600,042 A | 2/1997 | Chen et al. | 570/230 |
| 5,607,890 A | 3/1997 | Chen et al. | 205/202 |
| 5,646,304 A | 7/1997 | Acharya et al. | 549/259 |
| 5,663,112 A | 9/1997 | Ahn et al. | 502/304 |
| 5,663,465 A | 9/1997 | Clegg et al. | 570/224 |
| 5,663,472 A | 9/1997 | Benson et al. | 585/641 |
| 5,705,728 A | 1/1998 | Viswanathan et al. | 585/641 |
| 5,728,905 A | 3/1998 | Clegg et al. | 570/224 |
| 5,762,894 A | 6/1998 | Takatori et al. | 423/263 |
| 5,763,710 A | 6/1998 | Clegg et al. | 570/224 |
| 5,773,383 A | 6/1998 | Suciu | 502/355 |
| 5,874,380 A | 2/1999 | Chen et al. | 502/217 |
| 5,877,371 A | 3/1999 | Chen et al. | 585/467 |
| 5,880,058 A | 3/1999 | Moriya et al. | 502/302 |
| 5,883,037 A | 3/1999 | Chopin et al. | 502/308 |
| 5,898,014 A | 4/1999 | Wu et al. | 502/302 |
| 5,905,177 A | 5/1999 | Seo et al. | 570/243 |
| 5,919,727 A | 7/1999 | Brezny | 502/304 |
| 5,922,639 A | 7/1999 | Alario et al. | 502/230 |
| 5,925,590 A | 7/1999 | White et al. | 502/302 |
| 5,935,897 A | 8/1999 | Trubenbach et al. | 502/527.14 |
| 5,935,898 A | 8/1999 | Trubenbach et al. | 502/527.14 |
| 5,945,370 A | 8/1999 | Yokoi et al. | 502/304 |
| 5,945,573 A | 8/1999 | Nappa et al. | 570/175 |
| 5,955,638 A | 9/1999 | Schoebrechts et al. | 570/232 |
| 5,969,195 A | 10/1999 | Stabel et al. | 568/697 |
| 5,972,827 A | 10/1999 | Petit et al. | 502/225 |
| 5,972,830 A | 10/1999 | Yoshida et al. | 502/304 |
| 5,994,260 A | 11/1999 | Bonneau et al. | 502/304 |
| 6,002,019 A | 12/1999 | Tamhankar et al. | 549/285 |
| 6,090,743 A | 7/2000 | Chopin et al. | 502/302 |
| 6,136,048 A | 10/2000 | Birchem et al. | 44/354 |
| 6,165,931 A | 12/2000 | Rao | 502/224 |
| 6,191,329 B1 | 2/2001 | Benje | 570/243 |
| 6,194,345 B1 | 2/2001 | Mangnus et al. | 502/224 |

OTHER PUBLICATIONS

G. Olah et al., Selective Monohalogenation of Methane over Supported Acid or Platinum Metal Catalysts and Hydrolysis of Methyl Halides over γ–Alumina–Supported Metal Oxide/Hydroxide Catalysts. A Feasible Path for the Oxidative Conversion of Methane into Methyl Alcohol/Dimethyl Ether, American Chemical Society, vol. 107, No. 24, pp. 7097–7105, 1985.

E. Fortini et al., Stabilization of the Active Phase by Interaction with the Support in $CuCl_2$ Oxychlorination Catalysts, Journal of Catalysis, vol. 99, pp. 12–18, 1986.

M. McDonald et al., Effects of Pressure on the Oxyhydrochlorination of Methane, Chemical Engineering Science, vol. 49, No. 24A, pp. 4627–4637, 1994.

K. Weissermel et al., "Industrial Organic Chemistry," $2^{nd}$ edition, VCH, Weinheim, pp. 168–175, 1993.

E. T. Lance et al., Preparation, Phase Equilibria, and Crystal Chemistry of Lanthanum, Praseodymium, and Neodymium Hydroxide Chlorides, Journal of Solid State Chemistry, vol. 17, pp. 55–60, 1976.

S. Lin et al, Oxidative Dehydrogenation of Ethane over Lanthanum–Substituted Layered Complex Bismuth Chloride Oxide Catalysts, The Chemical Society of Japan, Chemistry Letters 1997, pp. 901–902.

Poznanski, J., "A Study of the chlorination of lanthanum and neodymium oxides", Materials Science, XVII, 1992, pp. 99–104.

International Search Report, International application No.: PCT/US 00/27700, International filing date: Jun. 10, 2000.

International Search Report, International application No.: PCT/US 00/27701, International filing date filing date: Jun. 10, 2000.

International Search Report, International application No.: PCT/US 00/27689, International filing date: Jun. 10, 2000.

International Search Report, International application No.: PCT/US 00/27272, International filing date: Mar. 10, 2000.

International Search Report, International application No.: PCT/US 00/31490, International filig date: Nov. 16, 2000.

International Search Report, International application No.: PCT/US 00/31488, International filing date: Nov. 16, 2000.

"Oxidative Halogenation and Optional Dehydrogenation of C3+ Hydrocarbons", filed in the Unites States on May 23, 2001, U.S. Appl. No. 60/293,132, Applicant: Albert E. Schweizer et al.

Process for vinyl Chloride Manufacture from Ethane and Ethane with Secondary Refractive Consumption of Reactor Effluent HCl:, filed in the United States on May 23, 2001, U.S. Appl. 60/292,994, Applicant: William D. Clark et al.

"Production of Vinyl Halide from Single Carbon Feedstocks", filed in the United States on May 23, 2001, U.S. Appl. 60/292,945, Applicant: William D. Clark et al.

I. Fells, The Kinetics of the Hydrolysis of the Chlorinated Methanes, Fuel Society Journal, vol. 10, pp. 26–35, 1959.

W. Pieters et al., The Oxyhydrochlorination of Methane on Fumed Silica—Based $Cu^{+1}$, K, La Catalysts: I. Catalyst Synthesis, Applied Catalysis, vol. 11, pp. 35–48, 1984.

Wm. C. Conner, Jr., et al., The Oxyhydrochlorination of Methane on Fumed Silica–Based Cu, K, La Catalysts: II Gas Phase Stoichiometry, Applied Catalysis, vol. 11, pp. 49–58, 1984.

P. Chanaud, et al., Catalytic membrane reactor for oxidative coupling of methane. Part 1: preparation and characterization of LaOCl membranes, Catalysis Today, 25, 1995, pp. 225–230.

P. Chanaud et al., Study of lanthanum–based colloidal sols formation, Journal of Materials. Science, 29, 1994, pp. 4244–4251.

C. T. Au et al., The oxidative coupling of methane over $BaCO_3$/LaOCl catalysts, Applied Catalysis A: General, 159, 1997, pp. 133–145.

Bert M. Weckhuysen, et al., Destructive absorption of carbon tetrachloride on lanthanum and cerium oxides, Phys. Chem. Chem. Phys., 1999, 1, pp. 3157–3162.

PROCESS FOR VINYL CHLORIDE MANUFACTURE FROM ETHANE AND ETHYLENE WITH PARTIAL CHL RECOVERY FROM REACTOR EFFLUENT

CROSS-REFERENCE TO RELATED APPLICATIONS

This application is a 371 of International Patent Application Serial Number PCT/US00/27701, filed Oct. 6, 2000, which claims the benefit of US provisional application serial number 60/166,897, filed Nov. 22, 1999. This application also claims the benefit of International Patent Application serial number PCT/US00/27272, filed Oct. 3, 2000.

This invention is directed to an apparatus and process for producing vinyl chloride monomer (VCM) from ethane and ethylene. Especially, this invention is directed to processes for producing vinyl chloride monomer where (1) significant quantities of both ethane and ethylene are present in input streams to the affiliated reactor, (2) hydrogen chloride in the reactor effluent is only partially recovered from the effluent in the first unit operation after the ethane/ethylene-to-vinyl reaction step or stage, and (3) a portion of the remainder of the hydrogen chloride is recycled in a recycle gas stream to the reactor.

Vinyl chloride is a key material in modern commerce, and most processes deployed today derive vinyl chloride from 1,2-dichloroethane (EDC) where the EDC is first-derived from ethylene; so, from an abstracted reference frame, at least a three-operation overall system is used (ethylene from primary hydrocarbons, preponderantly via thermal cracking; ethylene to EDC; and then EDC to vinyl chloride). There is an inherent long-felt need in the industry to move toward an approach where vinyl chloride is derived more directly and economically from primary hydrocarbons without a need to first manufacture and purify ethylene, and the inherent economic benefit related to this vision has inspired a significant amount of development.

As a first general area of development, ethane-to-vinyl manufacture is of interest to a number of firms engaged in vinyl chloride production, and a significant amount of literature on the subject is now available. The following paragraphs overview key work related to the embodiments presented in the new developments of the present disclosure.

GB Patent 1,039,369 entitled "CATALYTIC CONVERSION OF ETHANE TO VINYL CHLORIDE" which issued on Aug. 17, 1966 describes use of multivalent metals, including those in the lanthanum series, in the production of vinyl chloride from ethane. The patent describes use of certain catalysts provided that "steam, available chlorine and oxygen are used in specific controlled ratios." The described system operates at a temperature of between 500 and 750° C. Available chlorine in the described technology optionally includes 1,2-dichloroethane.

GB Patent 1,492,945 entitled "PROCESS FOR PRODUCING VINYL CHLORIDE" which issued on Nov. 23, 1977 to John Lynn Barclay discloses a process for the production of vinyl chloride using lanthanum in a copper-based ethane-to-vinyl catalyst. The authors describe that the lanthanum is present to favorably alter the volatility of copper at the elevated temperature required for operation. Examples show the advantage of excess hydrogen chloride in the affiliated reaction.

GB Patent 2,095,242 entitled "PREPARATION OF MONOCHLORO-OLEFINS BY OXYCHLORINATION OF ALKANES" which issued on Sep. 29, 1982 to David Roger Pyke and Robert Reid describes a "process for the production of monochlorinated olefins which comprises bringing into reaction at elevated temperature a gaseous mixture comprising an alkane, a source of chlorine and molecular oxygen in the presence of a . . . catalyst comprising metallic silver and/or a compound thereof and one or more compounds of manganese, cobalt or nickel". The authors indicate that mixtures of ethane and ethylene can be fed to the catalyst. No examples are given and the specific advantages of ethane/ethylene mixtures are not disclosed.

GB Patent 2,101,596 entitled "OXYCHLORINATION OF ALKANES TO MONOCHLORINATED OLEFINS" which issued on Jan. 19, 1983 to Robert Reid and David Pyke describes a "process for the production of monochlorinated olefins which comprises bringing into reaction at elevated temperature a gaseous mixture comprising an alkane, a source of chlorine and molecular oxygen in the presence of a . . . catalyst comprising compounds of copper, manganese and titanium and is useful in the production of vinyl chloride from ethane." The authors further describe that "the products of reaction are, in one embodiment, isolated and used as such or are, in one embodiment, recycled . . . to the reactor . . . to increase the yield of monochlorinated olefin." The authors indicate that mixtures of ethane and ethylene can be fed to the catalyst. No examples are given and the specific advantages of ethane/ethylene mixtures are not disclosed.

U.S. Pat. No. 3,629,354 entitled "HALOGENATED HYDROCARBONS" which issued on Dec. 21, 1971 to William Q. Beard, Jr. describes a process for the production of vinyl chloride and the co-production of ethylene from ethane in the presence of hydrogen chloride and oxygen. Preferred catalysts are supported copper or iron. An example in this patent shows excess hydrogen chloride (HCl) relative to ethane in the reaction. A ratio of one ethane to four hydrogen chlorides is used to produce a stream containing 38.4 percent ethylene (which requires no HCl to produce) and 27.9 percent vinyl chloride (which requires only one mole of HCl per mole of vinyl chloride to produce).

U.S. Pat. No. 3,658,933 entitled "ETHYLENE FROM ETHANE, HALOGEN AND HYDROGEN HALIDE THROUGH FLUIDIZED CATALYST" which issued on Apr. 25, 1972 to William Q. Beard, Jr. describes a process for production of vinyl halides in a three reactor system combining an oxydehydrogenation reactor, an oxyhalogenation reactor and a dehydrohalogenation reactor. The authors show that (oxy)halodehydrogenation of ethane is, in some cases, enhanced by addition of both halogen and hydrogen halide. As in U.S. Pat. No. 3,629,354, the ethylene generated produces VCM through conventional oxyhalogenation (oxychlorination) and cracking. HCl produced in the cracking operation is returned to the halodehydrogenation reactor.

U.S. Pat. No. 3,658,934 entitled "ETHYLENE FROM ETHANE AND HALOGEN THROUGH FLUIDIZED RARE EARTH CATALYST" which issued on Apr. 25, 1972 to William Q. Beard, Jr. and U.S. Pat. No. 3,702,311 entitled "HALODEHYDROGENATION CATALYST" which issued on Nov. 7, 1972 to William Q. Beard, Jr. both describe a process for production of vinyl halides in a three reactor system combining a halodehydrogenation reactor, an oxyhalogenation reactor and a dehydrohalogenation reactor. The authors describe the halodehydrogenation of ethane to produce ethylene for subsequent conversion to EDC through oxyhalogenation (oxychlorination) with subsequent production of VCM through conventional thermal cracking. HCl produced in the cracking operation is returned to the oxyhalogenation reactor in '934 and to the halodehydrogenation reactor in '311. In the latter patent, the advantages of excess total chlorine, as both HCl and $Cl_2$ are shown to augment yield of desirable products.

U.S. Pat. No. 3,644,561 entitled "OXYDEHYDROGENATION OF ETHANE" which issued on Feb. 22, 1972 to William Q. Beard, Jr. and U.S. Pat. No. 3,769,362 entitled "OXYDEHYDROGENATION OF ETHANE" which issued on Oct. 30, 1973 to William Q. Beard, Jr. relate closely to those above and describe processes for the oxydehydrogenation of ethane to ethylene in the presence of excess quantities of hydrogen halide. The patent describes a catalyst of either copper or iron halide further stabilized with rare earth halide where the ratio of rare earth to copper or iron halide is greater than 1:1. The patent describes use of a substantial excess of HCl relative to the molar amount of ethane fed, the HCl being unconsumed in the reaction.

U.S. Pat. No. 4,046,823 entitled "PROCESS FOR PRODUCING 1,2-DICHLOROETHANE" which issued on Sep. 6, 1977 to Ronnie D. Gordon and Charles M. Starks describes a process for the production of EDC where ethane and chlorine are reacted in the gas-phase over a copper containing catalyst.

U.S. Pat. No. 4,100,211 entitled "PROCESS FOR PREPARATION OF ETHYLENE AND VINYL CHLORIDE FROM ETHANE" which issued on Jul. 11, 1978 to Angelo Joseph Magistro describes regeneration of an iron catalyst for a process which reacts ethane into both ethylene and VCM in a mixture. This patent describes that a chlorine source is present from 0.1 mole to 10 moles per mole of ethane. In general, as the ratio of hydrogen chloride to ethane is increased, the yield of vinyl chloride and other chlorinated products also increases even as the yield of ethylene decreases.

U.S. Pat. No. 4,300,005 entitled "PREPARATION OF VINYL CHLORIDE" which issued on Nov. 10, 1981 to Tao P. Li suggests a copper-based catalyst for production of VCM in the presence of excess HCl.

U.S. Pat. No. 5,097,083 entitled "PROCESS FOR THE CHLORINATION OF ETHANE" which issued on Mar. 17, 1992 to John E. Stauffer describes chlorocarbons as a chlorine source in an ethane-to-VCM process. This patent describes methods where chlorohydrocarbons may be used to capture HCl for subsequent use in the production of vinyl.

EVC Corporation has been active in ethane-to-vinyl technology, and the following four patents have resulted from their efforts in development.

EP 667,845 entitled "OXYCHLORINATION CATALYST" which issued on Jan. 14, 1998 to Ray Hardman and Ian Michael Clegg describes a copper-based catalyst with a stabilization package for ethane-to-vinyl catalysis. This catalyst appears to be relevant to the further technology described in the following three US patents.

U.S. Pat. No. 5,663,465 entitled "BY-PRODUCT RECYCLING IN OXYCHLORINATION PROCESS" which issued on Sep. 2, 1997 to Ian Michael Clegg and Ray Hardman describes a method for the catalytic oxychlorination of ethane to VCM which combines ethane and a chlorine source in an oxychlorination reactor with a suitable catalyst; recycles the byproducts to the oxychlorination reactor; treats unsaturated chlorinated hydrocarbon byproducts in a hydrogenation step to convert them to their saturated counterparts and passes them back to the reactor; and chlorinates ethylene byproduct to 1,2-dichloroethane for recycle.

U.S. Pat. No. 5,728,905 entitled "VINYL CHLORIDE PRODUCTION PROCESS" which issued on Mar. 17, 1998 to Ian Michael Clegg and Ray Hardman discusses ethane-to-vinyl manufacture in the presence of excess HCl using a copper catalyst. The patent describes a process of catalytic oxychlorination of ethane between ethane, an oxygen source and a chlorine source in the presence of a copper and alkali metal-containing catalyst. HCl is supplied to the oxychlorination reactor in excess of the stoichiometric requirement for chlorine.

U.S. Pat. No. 5,763,710 entitled "OXYCHLORINATION PROCESS" which issued on Jun. 9, 1998 to Ian Michael Clegg and Ray Hardman discusses catalytic oxychlorination of ethane to VCM by combining ethane and a chlorine source in an oxychlorination reactor in the presence of an oxychlorination catalyst (the reaction conditions selected to maintain an excess of HCl); separating the VCM products; and recycling by-products to the reactor.

Turning now to art in the derivation of vinyl chloride from ethylene, most commercial processes for the production of VCM use ethylene and chlorine as key raw materials. Ethylene is contacted with chlorine in liquid 1,2-dichloroethane containing a catalyst in a direct chlorination reactor. The 1,2-dichloroethane is subsequently cracked at elevated temperature to yield VCM and hydrogen chloride (HCl). The HCl produced is in turn fed to an oxychlorination reactor where it is reacted with ethylene and oxygen to yield more 1,2-dichloroethane. This 1,2-dichloroethane is also fed to thermal cracking to produce VCM. Such a process is described in U.S. Pat. No. 5,210,358 entitled "CATALYST COMPOSITION AND PROCESS FOR THE PREPARATION OF ETHYLENE FROM ETHANE" which issued on May 11, 1993 to Angelo J. Magistro.

The three unit operations (direct chlorination, oxychlorination and thermal cracking) of most presently used commercial processes are frequently referenced in combination as a "balanced" EDC plant, although additional sources of chlorine (HCl) are, in one embodiment, also brought into these extended plant systems. The net stoichiometry of the "balanced" plant is:

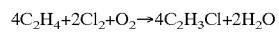

$$4C_2H_4 + 2Cl_2 + O_2 \rightarrow 4C_2H_3Cl + 2H_2O$$

Ethylene cost represents a significant fraction of the total cost of production of VCM and requires expensive assets to produce. Ethane is less expensive than ethylene, and production of VCM from ethane should, therefore, reasonably lower the production cost of VCM in comparison to the production cost of VCM when manufactured primarily from purified and separated ethylene.

It is common to refer to the conversion of ethylene, oxygen and hydrogen chloride to 1,2-dichloroethane as oxychlorination. Catalysts for the production of 1,2-dichloroethane by oxychlorination of ethylene share many common characteristics. Catalysts capable of performing this chemistry have been classified as modified Deacon catalysts [Olah, G. A., Molnar, A., Hydrocarbon Chemistry, John Wiley & Sons (New York, 1995), pg 226]. Deacon chemistry refers to the Deacon reaction, the oxidation of HCl to yield elemental chlorine and water. Other authors have offered that oxychlorination is the utilization of HCl for chlorination and that the HCl is converted oxidatively into $Cl_2$ by means of the Deacon process [*Selective Oxychlorination of Hydrocarbons: A Critical Analysis*, Catalytica Associates, Inc., Study 4164A, October 1982, page 1]. The ability of oxychlorination catalysts to produce free chlorine ($Cl_2$) thus defines them. Indeed, oxychlorination of alkanes has been linked to the production of free chlorine in the system [*Selective Oxychlorination of Hydrocarbons: A*

*Critical Analysis*, Catalytical Associates, Inc., Study 4164A, October 1982, page 21 and references therein]. These catalysts employ supported metals capable of accessing more than one stable oxidation state, such as copper and iron. In the conventional technology, oxychlorination is the oxidative addition of two chlorine atoms to ethylene from HCl or another reduced chlorine source.

Production of vinyl from ethane can proceed via oxychlorination provided catalysts are present which are capable of production of free chlorine. Such catalysts will convert ethylene to 1,2-dichloroethane at low temperatures. At higher temperatures, 1,2-dichloroethane will be disposed to thermally crack to yield HCl and vinyl chloride. Oxychlorination catalysts chlorinate olefinic materials to still higher chlorocarbons. Thus, just as ethylene is converted to 1,2-dichloroethane, vinyl chloride is converted to 1,1,2-trichloroethane. Processes using oxychlorination catalysts inherently produce higher chlorinated side-products. This is examined in great detail in patents to EVC (EP 667,845, U.S. Pat. No. 5,663,465, U.S. Pat. No. 5,728,905, and U.S. Pat. No. 5,763,710), which show high levels of multichlorinated side-products being produced over the oxychlorination catalyst used. In consideration of the above, a number of concepts regarding the use of ethane to produce VCM have clearly been described previously. Catalysts employed most frequently are modified Deacon catalysts operated at sufficiently higher temperatures (>400° C.) than those required to perform ethylene oxychlorination (<275° C.). Catalysts used for ethane-to-VCM manufacture are frequently stabilized against the migration of the first-row transition metals, as described and reviewed in GB Patent 1,492,945; GB Patent 2,101,596; U.S. Pat. No. 3,644,561; U.S. Pat. No. 4,300,005; and U.S. Pat. No. 5,728,905.

Use of chlorocarbons as chlorine sources in ethane-to-VCM processes has been disclosed in GB Patent 1,039,369; GB Patent 2,101,596; U.S. Pat. No. 5,097,083; U.S. Pat. No. 5,663,465; and U.S. Pat. No. 5,763,710. GB Patent 1,039,369 requires that water be fed to the reactor system. GB Patent 2,101,596 is specific to copper catalysts. U.S. Pat. No. 5,663,465 describes a process which uses a direct chlorination step to convert ethylene to EDC prior to feeding it back to the VCM reactor.

Notwithstanding a relatively qualitative reference in GB Patent 2,095,242, another recent development in ethylene-to-vinyl processes is outlined in Dow Case No. 44649 to Mark E. Jones, Michael M. Olken, and Daniel A. Hickman, entitled "A PROCESS FOR THE CONVERSION OF ETHYLENE TO VINYL CHLORIDE, AND NOVEL CATALYST COMPOSITIONS USEFUL FOR SUCH PROCESS", filed on Oct. 3, 2000 in the United States Receiving Office, Express Mail Mailing Number EL636832801US. The catalyst of this application demonstrates utility in reacting significant quantities of both ethane and ethylene into vinyl chloride monomer and thereby opens a door to new approaches in processes for vinyl chloride manufacture. However, the catalyst action yields hydrogen chloride in the reaction product. In this regard, management of hydrogen chloride (and affiliated hydrochloric acid) within the process is a key issue to be resolved when a catalyst system capable of conversion of both ethane and ethylene into vinyl chloride monomer is used. In contemplation of vinyl chloride facility construction, there is also a need to enable use of prior equipment as much as possible, where some existing equipment may have the ability to handle hydrogen chloride and other existing equipment does not have the ability to handle hydrogen chloride. The present invention provides embodiments for fulfilling these needs, by providing an apparatus and process for handling hydrogen chloride generated from the ethane/ethylene-to-vinyl reactor by essentially fully recovering it from the reactor effluent in the first unit operation after the ethane/ethylene-to-vinyl reaction step or stage.

The invention provides a method of manufacturing vinyl chloride, using the steps of:
generating a reactor effluent stream by catalytically reacting together ethane, ethylene, oxygen, and at least one chlorine source of hydrogen chloride, chlorine, or a chlorohydrocarbon, where the molar ratio of the ethane to the ethylene is between 0.02 and 50;
cooling and condensing the reactor effluent stream to provide a raw product stream having a first portion of the hydrogen chloride and a raw cooled hydrogen chloride stream having a second portion of the hydrogen chloride;
separating the raw product stream into a vinyl chloride monomer product stream and into a lights stream having the first portion of the hydrogen chloride; and
recycling the lights stream to catalytically react together with the ethane, the ethylene, the oxygen, and the chlorine source in the generating step.

The invention also provides a method of manufacturing vinyl chloride, comprising the steps of:
generating a reactor effluent stream by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
cooling and condensing said reactor effluent stream to provide a raw product stream having a first portion of said hydrogen chloride and a raw cooled hydrogen chloride stream having a second portion of said hydrogen chloride;
separating said raw product stream into a vinyl chloride monomer product stream and into a lights stream having said first portion of said hydrogen chloride; and
recycling said lights stream to catalytically react together with said ethane, said ethylene, said oxygen, and said chlorine source in said generating step.

The invention further provides a method of manufacturing vinyl chloride, comprising the steps of:
generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
cooling and condensing said reactor effluent stream to provide a raw product stream having a first portion of said hydrogen chloride and a raw cooled hydrogen chloride stream having a second portion of said hydrogen chloride;
separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;
recovering an anhydrous hydrogen chloride stream from said raw cooled hydrogen chloride stream;
recycling said anhydrous hydrogen chloride stream to said reactor as said hydrogen chloride reactant; and
recycling said lights stream to said reactor.

The invention further provides a method of manufacturing vinyl chloride, comprising the steps of:
generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;

cooling and condensing said reactor effluent stream to provide a raw product stream having a first portion of said hydrogen chloride and a raw cooled hydrogen chloride stream having a second portion of said hydrogen chloride;
separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;
recovering an anhydrous hydrogen chloride stream from said raw cooled hydrogen chloride stream;
recycling said anhydrous hydrogen chloride stream to said reactor as said hydrogen chloride reactant;
dividing said lights stream into a purge stream and a recycle gas stream;
absorbing hydrogen chloride from said purge stream to separate an aqueous hydrogen chloride stream;
combining said aqueous hydrogen chloride stream with said raw cooled hydrogen chloride stream;
absorbing and recycling to said reactor a C2 stream from said purge stream; and
recycling said recycle gas stream to said reactor.

The invention further provides a method of manufacturing vinyl chloride, comprising the steps of:
generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
cooling and condensing said reactor effluent stream to provide a raw product stream having a first portion of said hydrogen chloride and a raw cooled hydrogen chloride stream having a second portion of said hydrogen chloride;
separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;
recovering an anhydrous hydrogen chloride stream from said raw cooled hydrogen chloride stream;
recycling said anhydrous hydrogen chloride stream to said reactor as said hydrogen chloride reactant;
dividing said lights stream into a purge stream and a recycle gas stream;
absorbing hydrogen chloride from said purge stream to separate an aqueous hydrogen chloride stream;
combining said aqueous hydrogen chloride stream with said raw cooled hydrogen chloride stream;
hydrogenating said cis-1,2-dichloroethylene and trans-1,2-dichloroethylene blended stream to provide recycle feed to said reactor,
absorbing and recycling to said reactor a C2 stream from said purge stream; and
recycling said recycle gas stream to said reactor.

The invention further provides an apparatus for manufacturing vinyl chloride, comprising:
a reactor for generating a reactor effluent stream by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
means for cooling and condensing said reactor effluent stream to provide a raw product stream having a first portion of said hydrogen chloride and a raw cooled hydrogen chloride stream having a second portion of said hydrogen chloride;
means for separating said raw product stream into a vinyl chloride monomer product stream and into a lights stream having said first portion of said hydrogen chloride; and
means for recycling said lights stream to said reactor.

The invention further provides an apparatus for manufacturing vinyl chloride, comprising:
a reactor for generating a reactor effluent stream by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
means for cooling and condensing said reactor effluent stream to provide a raw product stream having a first portion of said hydrogen chloride and a raw cooled hydrogen chloride stream having a second portion of said hydrogen chloride;
means for separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;
means for recovering an anhydrous hydrogen chloride stream from said raw cooled hydrogen chloride stream;
means for recycling said anhydrous hydrogen chloride stream to said reactor as said hydrogen chloride reactant; and
means for recycling said lights stream to said reactor.

The invention further provides an apparatus for manufacturing vinyl chloride, comprising:
a reactor for generating a reactor effluent stream by catalytically reacting together, ethane, ethylene, oxygen, and at least one chlorine source of hydrogen chloride, chlorine, or a chlorohydrocarbon, wherein the molar ratio of said ethane to said ethylene is between 0.02 and 50;
means for cooling and condensing said reactor effluent stream to provide a raw product stream having a first portion of said hydrogen chloride and a raw cooled hydrogen chloride stream having a second portion of said hydrogen chloride;
means for separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;
means for recovering an anhydrous hydrogen chloride stream from said raw cooled hydrogen chloride stream;
means for recycling said anhydrous hydrogen-chloride stream to said reactor as said hydrogen chloride reactant;
means for dividing said lights stream into a purge stream and a recycle gas stream;
means for absorbing hydrogen chloride from said purge stream to separate an aqueous hydrogen chloride stream;
means for combining said aqueous hydrogen chloride stream with said raw cooled hydrogen chloride stream;
means for absorbing and recycling to said reactor a C2 stream from said purge stream; and
means for recycling said recycle gas stream to said reactor.

The invention further provides an apparatus for manufacturing vinyl chloride, comprising:
a reactor for generating a reactor effluent stream by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
means for cooling and condensing said reactor effluent stream to provide a raw product stream having a first portion of said hydrogen chloride and a raw cooled hydrogen chloride stream having a second portion of said hydrogen chloride;

means for separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;

means for recovering an anhydrous hydrogen chloride stream from said raw cooled hydrogen chloride stream;

means for recycling said anhydrous hydrogen chloride stream to said reactor as said hydrogen chloride reactant;

means for dividing said lights stream into a purge stream and a recycle gas stream;

means for absorbing hydrogen chloride from said purge stream to separate an aqueous hydrogen chloride stream;

means for combining said aqueous hydrogen chloride stream with said raw cooled hydrogen chloride stream;

means for hydrogenating said cis-1,2-dichloroethylene and trans-1,2-dichloroethylene blended stream to provide recycle feed to said reactor;

means for absorbing and recycling to said reactor a C2 stream from said purge stream; and means for recycling said recycle gas stream to said reactor.

The invention further provides vinyl chloride manufactured using a process comprising the steps of:

generating a reactor effluent stream by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;

cooling and condensing said reactor effluent stream to provide a raw product stream having a first portion of said hydrogen chloride and a raw cooled hydrogen chloride stream having a second portion of said hydrogen chloride;

separating said raw product stream into a vinyl chloride monomer product stream and into a lights stream having said first portion of said hydrogen chloride; and recycling said lights stream to catalytically react together with said ethane, said ethylene, said oxygen, and said chlorine source in said generating step.

The invention further provides vinyl chloride manufactured using a process comprising the steps of:

generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;

cooling and condensing said reactor effluent stream to provide a raw product stream having a first portion of said hydrogen chloride and a raw cooled hydrogen chloride stream having a second portion of said hydrogen chloride;

separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;

recovering an anhydrous hydrogen chloride stream from said raw cooled hydrogen chloride stream;

recycling said anhydrous hydrogen chloride stream to said reactor as said hydrogen chloride reactant; and recycling said lights stream to said reactor.

The invention further provides vinyl chloride manufactured using a process comprising the steps of:

generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;

cooling and condensing said reactor effluent stream to provide a raw product stream having a first portion of said hydrogen chloride and a raw cooled hydrogen chloride stream having a second portion of said hydrogen chloride;

separating said raw product stream into a water product stream, a vinyl chloride monomer product stream, an ethyl chloride stream, a cis-1,2 dichloroethylene and trans-1,2-dichloroethylene blended stream, a 1,2-dichloroethane stream, a heavies stream, and a lights stream having said first portion of said hydrogen chloride;

recovering an anhydrous hydrogen chloride stream from said raw cooled hydrogen chloride stream;

recycling said anhydrous hydrogen chloride stream to said reactor as said hydrogen chloride reactant;

dividing said lights stream into a purge stream and a recycle gas stream;

absorbing hydrogen chloride from said purge stream to separate an aqueous hydrogen chloride stream;

combining said aqueous hydrogen chloride stream with said raw cooled hydrogen chloride stream;

absorbing and recycling to said reactor a C2 stream from said purge stream; and recycling said recycle gas stream to said reactor.

The invention further provides vinyl chloride manufactured using a process comprising the steps of:

generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;

cooling and condensing said reactor effluent stream to provide a raw product stream having a first portion of said hydrogen chloride and a raw cooled hydrogen chloride stream having a second portion of said hydrogen chloride;

separating said raw product stream into a water product stream a vinyl chloride monomer product stream, an ethyl, chloride stream, a cis-1,2-dichloroethylene and trans-1,2-dichloroethylene blended stream, a 1,2-dichloroethane stream, a heavies stream, and a lights stream having said first portion of said hydrogen chloride;

recovering an anhydrous hydrogen chloride stream from said raw cooled hydrogen chloride stream;

recycling said anhydrous hydrogen chloride stream to said reactor as said hydrogen chloride reactant;

dividing said lights stream into a purge stream and a recycle gas stream;

absorbing hydrogen chloride from said purge stream to separate an aqueous hydrogen chloride stream;

combining said aqueous hydrogen chloride stream with said raw cooled hydrogen chloride stream;

hydrogenating said cis-1,2-dichloroethylene and trans-1,2-dichloroethylene blended stream to provide recycle feed to said reactor;

absorbing and recycling to said reactor a C2 stream from said purge stream; and recycling said recycle gas stream to said reactor.

Additional features and advantages of the present invention are more fully apparent from a reading of the detailed description of the preferred embodiments and the accompanying drawings in which:

As noted in the Background discussion of the present specification, oxychlorination is conventionally referenced as the oxidative addition of two chlorine atoms to ethylene from HCl or other reduced chlorine source. Catalysts capable of performing this chemistry have been classified as modified Deacon catalysts [Olah, G. A., Molnar, A., Hydrocarbon Chemistry, John Wiley & Sons (New York, 1995), pg 226]. Deacon chemistry refers to the Deacon reaction, the oxidation of HCl to yield elemental chlorine and water.

In contrast to oxychlorination, the preferred process described herein preferably utilizes oxydehydro-chlorination in converting ethane-containing and ethylene-containing streams to VCM at high selectivity. Oxydehydro-chlorination is the conversion of a hydrocarbon, using oxygen and a chlorine source, to a chlorinated hydrocarbon wherein the carbons either maintain their initial valence or have their valency reduced (that is, $sp^3$ carbons remain $sp^3$ or are converted to $sp^2$, and $sp^2$ carbons remain $sp^2$ or are converted to sp). This differs from the conventional definition of oxychlorination whereby ethylene is converted to 1,2-dichloroethane, using oxygen and a chlorine source, with a net increase in carbon valency (that is, $sp^2$ carbons are converted to $sp^3$ carbons). Given the ability of the catalyst to convert ethylene to vinyl chloride, it is advantageous to recycle ethylene produced in the oxydehydro-chlorination reaction process back to the reactor. The byproducts produced in the oxydehydro-chlorination reactor include ethyl chloride, 1,2-dichloroethane, cis-1,2-dichloroethylene and trans-1,2-dichloroethylene. The oxydehydro-chlorination catalyst is also an active catalyst for the elimination of HCl from saturated chlorohydrocarbons. Recycle of ethyl chloride and 1,2-dichloroethane is, in some cases, advantageously employed in the production of vinyl chloride. The remaining significant chlorinated organic side-products are the dichloroethylenes. These materials are, in one embodiment, hydrogenated to yield 1,2-dichloroethane. 1,2-dichloroethane is a large volume chemical and is either sold or recycled. In an alternative embodiment, EDC is hydrogenated completely to yield ethane and HCl. Intermediate severity hydrogenations yield mixtures of 1,2-dichloroethane, ethane, ethyl chloride, and HCl; such mixtures are also appropriate for recycle to the oxydehydro-chlorination reactor.

Figure 1:
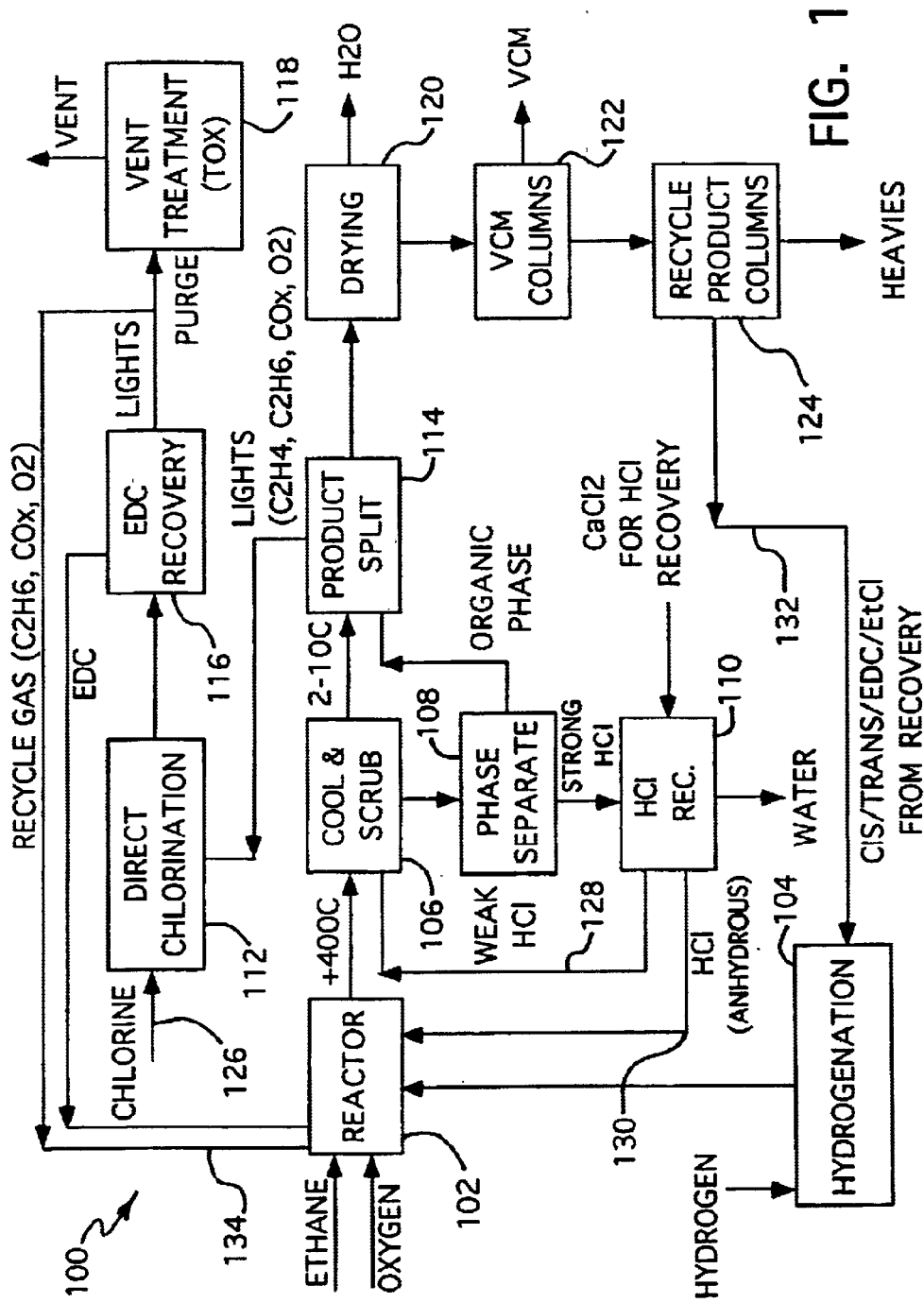
FIG. 1 shows characterization, as best understood from earlier publications, of a contemplated ethane-to-vinyl chloride process employing a catalyst capable of converting ethane to VCM.

Turning now to consideration of FIG. 1, for ethane-to-vinyl conversion as best understood from earlier publications, Ethane to VCM Process 100 shows characterization of a contemplated ethane-to-vinyl chloride process employing a catalyst capable of converting ethane to VCM; in this regard, the process does not provide for input of significant quantities of ethylene from either recycle streams or feed-streams to the ethane-VCM reactor (Ethane Reactor 102). It should also be noted that, since an ethane-to-vinyl manufacturing system of appropriate normal manufacturing scale has not, to the best knowledge of the inventors, been yet constructed, proposed process approaches are the only sources for embodiments which have been previously conceptualized. In this regard, Process 100 is a unified and simplified approximation to processes collectively reviewed in several publications respective to investigations and developments at EVC Corporation: Vinyl Chloride/Ethylene Dichloride 94/95-5 (August, 1996; Chemical Systems, Inc.; Tarrytown, N.Y.); EP 667,845; U.S. Pat. No. 5,663,465; U.S. Pat. No. 5,728,905; and U.S. Pat. No. 5,763,710.

In consideration of the details shown in FIG. 1, Ethane Reactor 102 outputs a fluid stream to Quench Column 106 where HCl is quenched from the reactor output effluent. Quench Column 106 forwards a raw strong HCl aqueous stream to Phase Separation Subsystem 108. Phase Separation Subsystem 108 outputs a fluid stream to Anhydrous HCl Recovery Subsystem 110 where aqueous hydrogen chloride (hydrochloric acid), anhydrous HCl, and water are separated from the raw strong HCl aqueous stream.

Anhydrous HCl Recovery Subsystem 110 outputs Stream 130 to recycle anhydrous hydrogen chloride to Ethane Reactor 102, and Anhydrous HCl Recovery Subsystem 110 also outputs water (for subsequent use or to waste recovery). Anhydrous HCl Recovery Subsystem 110 returns a relatively dilute aqueous stream of HCl (hydrochloric acid) via Stream 128 to Quench Column 106. Quench Column 106 also outputs a fluid stream to Lights Column 114 where a lights stream containing ethylene is further removed from the reactor effluent product stream.

Lights Column 114 outputs the lights stream to Direct Chlorination Reactor 112 where chlorine (Stream 126) is added to directly chlorinate ethylene in the lights stream into EDC (1,2-dichloroethane). EDC is recovered in EDC Recovery Column 116 for recycle to Ethane Reactor 102, and a certain amount of the remaining lights gas is recycled to Ethane Reactor 102 as Stream 134 with CO (carbon monoxide) composition instrumentation providing a measurement (not shown) for use in a control system's (not shown) determination of an appropriate portion of the remaining lights gas for processing via Vent Oxidation Unit 118 to generate a vent stream for removal of CO, $CO_2$, and other impurities from the system.

Effluent from Lights Column 114 which does not proceed to Direct Chlorination Reactor 112 forwards (a) first, to Drying Subsystem 120 for removal of water; (b) further, to VCM Purification Column 122 for separation of VCM (vinyl chloride monomer) product; and then (c) further, to Heavies Column 124 for removal of heavies and generation of Stream 132. Stream 132 is a blended fluid of cis-1,2-dichloroethylene and trans-1,2-dichloroethylene, 1,2-dichloroethane, ethyl chloride, and other chlorinated organics. In an alternative contemplated embodiment based upon consideration of the literature, Drying Subsystem 120 removes water prior to Lights Column 114, with the VCM-carrying effluent from Lights Column 114 being forwarded (a) first, to VCM Purification Column 122 for separation of VCM (vinyl chloride monomer) product and then (b) further, to Heavies Column 124 for removal of heavies and generation of Stream 132.

Finally, Stream 132 forwards to RCl (chlorinated organics) Hydrogenation Reactor 104 where addition of hydrogen effects a recycle stream for forwarding to Ethane Reactor 102.

Figure 2:
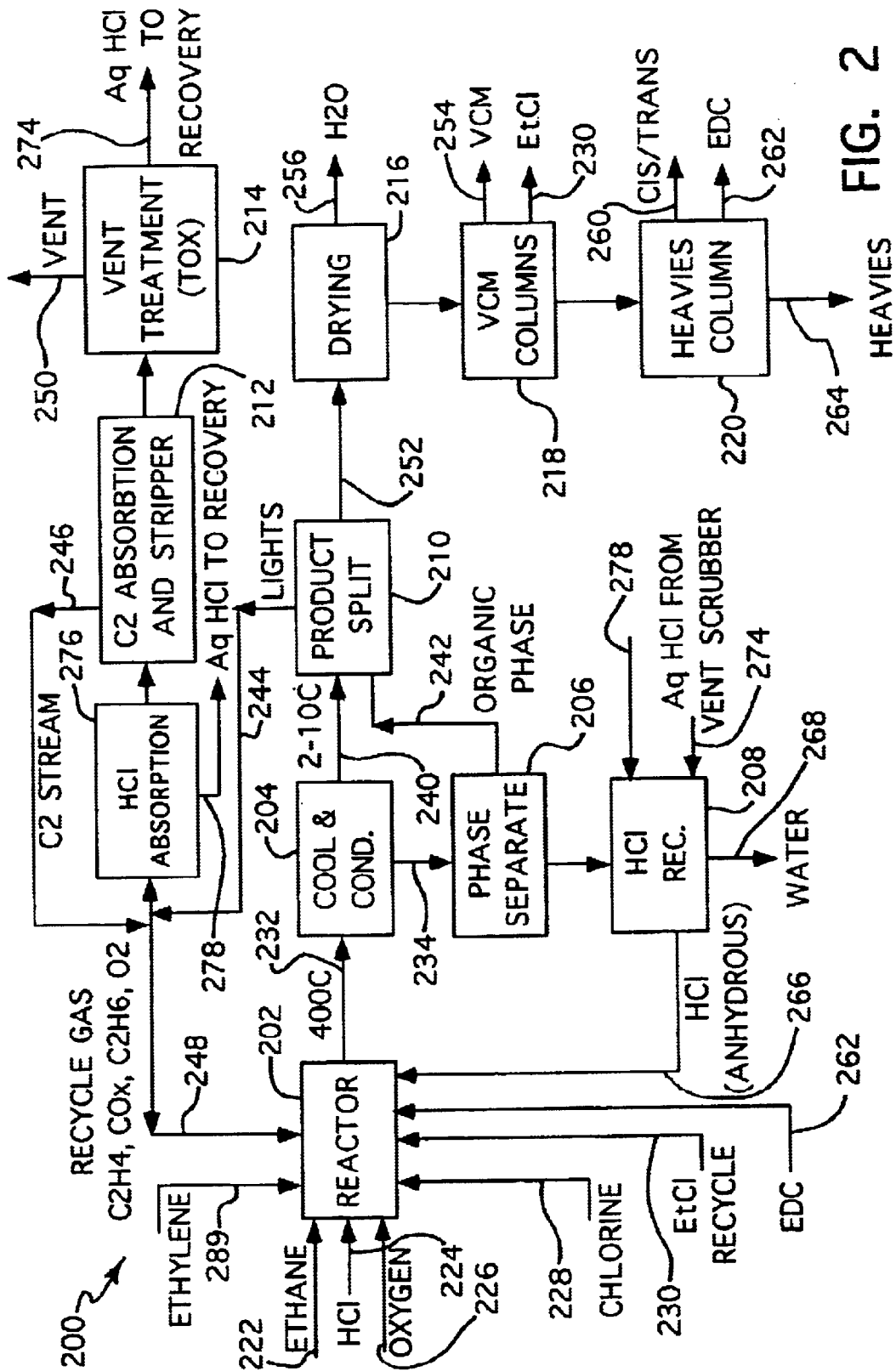
FIG. 2 shows an ethane/ethylene-to-vinyl chloride process employing a catalyst capable of converting ethane and ethylene to VCM via oxydehydro-chlorination.

Turning now to consideration of FIG. 2, according to the preferred embodiments of the present specification, Ethane to VCM Oxydehydro-chlorination Process 200 shows an ethane/ethylene-to-vinyl chloride process employing a catalyst capable of converting ethane and ethylene to VCM via oxydehydro-chlorination; in this regard, the process provides for input of significant quantities of both ethane and ethylene from either recycle streams or feed-streams to the reactor (Ethane/Ethylene To VCM Oxydehydro-chlorination Reactor 202). Ethane/Ethylene To VCM Oxydehydrochlorination Reactor 202 receives input from (a) feed streams Ethane Feed Stream 222, HCl Feed Stream 224, Oxygen Feed Stream 226, and Chlorine Feed Stream 228 and (b) recycle streams Ethyl Chloride Stream 230, Hydrogen chloride (HCl) Stream 266, and lights recycle Stream 248 as well a portion of EDC Stream 262 when EDC is advantageously used for recycle according to the market and operational conditions at a particular moment of manufacture.

As reflected in Dow Case No. 44649 to Mark E. Jones, Michael M. Olken, and Daniel A. Hickman, entitled "A PROCESS FOR THE CONVERSION OF ETHYLENE TO VINYL CHLORIDE, AND NOVEL CATALYST COMPOSTIONS USEFUL FOR SUCH PROCESS", filed on Oct. 3, 2000 in the United States Receiving Office, Express Mail Mailing Number EL636832801US, the catalyst used in Ethane/Ethylene To VCM Oxydehydro-chlorination Reactor 202 comprises at least one rare earth material. The rare earths are a group of 17 elements consisting of scandium (atomic number 21), yttrium (atomic number 39) and the lanthanides (atomic numbers 57–71) [James B. Hedrick, U.S. Geological Survey—Minerals Information—1997, "Rare-Earth Metals"]. The catalyst can be provided as either a porous, bulk material or it can be supported on a suitable support. Preferred rare earth materials are those based on lanthanum, cerium, neodymium, praseodymium, dysprosium, samarium, yttrium, gadolinium, erbium, ytterbium, holmium, terbium, europium, thulium, and lutetium. Most preferred rare earth materials for use in the aforementioned VCM process are based on those rare earth elements which are typically considered as being single valency materials. Catalytic performance of multi-valency materials appears to be less desirable than those that are single valency. For example, cerium is known to be an oxidation-reduction catalyst having the ability to access both the $3^+$ and $4^+$ stable oxidation states. This is one reason why, if the rare earth material is based on cerium, the catalyst further comprises at least one more rare earth element other than cerium. Preferably, if one of the rare earths employed in the catalyst is cerium, the cerium is provided in a molar ratio that is less than the total amount of other rare earths present in the catalyst. More preferably, however, substantially no cerium is present in the catalyst. By "substantially no cerium" it is meant that any cerium is in an amount less than 33 atom percent of the rare earth components, preferably less than 20 atom percent, and most preferably less than 10 atom percent.

The rare earth material for the catalyst is more preferably based upon lanthanum, neodymium, praseodymium or mixtures of these. Most preferably, at least one of the rare earths used in the catalyst is lanthanum. Furthermore, for the ethylene-containing feed to VCM process of this invention, the catalyst is substantially free of iron and copper. In general, the presence of materials that are capable of oxidation-reduction (redox) is undesirable for the catalyst. It is preferable for the catalyst to also be substantially free of other transition metals that have more than one stable oxidation state. For example, manganese is another transition metal that is preferably excluded from the catalyst. By "substantially free" it is meant that the atom ratio of rare earth element to redox metal in the catalyst is greater than 1, preferably greater than 10, more preferably greater than 15, and most preferably greater than 50.

As stated above, the catalyst may also be deposited on an inert support. Preferred inert supports include alumina, silica gel, silica-alumina, silica-magnesia, bauxite, magnesia, silicon carbide, titanium oxide, zirconium oxide, zirconium silicate, and combinations thereof. However, in a most preferred embodiment, the support is not a zeolite. When an inert support is utilized, the rare earth material component of the catalyst typically comprises from 3 weight percent (wt percent) to 85 wt percent of the total weight of the catalyst and support. The catalyst may be supported on the support using methods already known in the art.

It may also be advantageous to include other elements within the catalyst in both of the porous, bulk material and supported forms. For example, preferable elemental additives include alkaline earths, boron, phosphorous, sulfur, silicon, germanium, titanium, zirconium, hafnium, aluminum, and combinations thereof. These elements can be present to alter the catalytic performance of the composition or to improve the mechanical properties (for example attrition-resistance) of the material.

Prior to combining the ethylene-containing feed, oxygen source, and chlorine source in the reactor for the VCM process embodiment of this invention, it is preferable for the catalyst composition to comprise a salt of at least one rare earth element with the proviso that the catalyst is substantially free of iron and copper and with the further proviso that when cerium is employed the catalyst further comprises at least one more rare earth element other than cerium. The salt of at least one rare earth element is preferably selected from rare earth oxychlorides, rare earth chlorides, rare earth oxides, and combinations thereof, with the proviso that the catalyst is substantially free of iron and copper and with the further proviso that when cerium is used the catalyst further comprises at least one more rare earth element other than cerium. More preferably, the salt comprises a rare earth oxychloride of the formula MOCl, wherein M is at least one rare earth element chosen from lanthanum, cerium, neodymium, praseodymium, dysprosium, samarium, yttrium, gadolinium, erbium, ytterbium) holmium, terbium, europium, thulium, lutetium, or mixtures thereof, with the proviso that, when cerium is present, at least one more rare earth element other than cerium is also present. Most preferably, the salt is a porous, bulk lanthanum oxychloride (LaOCl) material. As has been mentioned, this material beneficially does not undergo gross changes (for example, fracturing) when chlorinated in situ in this process, and provides the further beneficial property of water solubility in the context of this process after a period of use (LaOCl is initially water-insoluble), so that should spent catalyst need to be removed from a fluidized bed, fixed bed reactor or other process equipment or vessels, this can be done without hydroblasting or conventional labor-intensive mechanical techniques by simply flushing the spent catalyst from the reactor in question with water.

Typically, when the salt is a rare earth oxychloride (MOCl), it has a BET surface area of at least 12 $m^2/g$, preferably at least 15 $m^2/g$, more preferably at least 20 $m^2/g$, and most preferably at least 30 $m^2/g$. Generally, the BET surface area is less than 200 $m^2/g$. For these above measurements, the nitrogen adsorption isotherm was measured at 77K and the surface area was calculated from the isotherm data utilizing the BET method (Branauer, S., Emmett, P. H., and Teller, E., J. Am. Chem. Soc., 60, 309 (1938)). In addition, it is noted that the MOCl phases possess characteristic powder X-Ray Diffraction (XRD) patterns that are distinct from the $MCl_3$ phases.

It is also possible, as indicated in several instances previously, to have mixtures of the rare earths ("M") within the MOCl composition. For example, M can be a mixture of at least two rare earths selected from lanthanum, cerium, neodymium, praseodymium, dysprosium, samarium, yttrium, gadolinium, erbium, ytterbium, holmium, terbium, europium, thulium and lutetium. Similarly, it is also possible to have mixtures of different MOCl compositions wherein M is different as between each composition of the MOCl's in the mixture.

Once the ethylene-containing feed, oxygen source, and chlorine source are combined in the reactor, a catalyst is formed in situ from the salt of at least one rare earth element. In this regard, it is believed that the in situ formed catalyst comprises a chloride of the rare earth component. An example of such a chloride is $MCl_3$, wherein M is a rare earth component selected from lanthanum, cerium, neodymium, praseodymium, dysprosium, samarium, yttrium, gadolinium, erbium, ytterbium, holmium, terbium, europium, thulium, lutetium and mixtures thereof, with the proviso that when cerium is present the catalyst further comprises at least one more rare earth element other than cerium. Typically, when the salt is a rare earth chloride ($MCl_3$), it has a BET surface area of at least 5 $m^2/g$, preferably at least 10 $m^2/g$, more preferably at least 15 $m^2/g$, more preferably at least 20 $m^2/g$, and most preferably at least 30 $m^2/g$.

In light of the disclosure herein, those of skill in the art will undoubtedly recognize alternative methods for preparing useful catalyst compositions. A method currently felt to be preferable for forming the composition comprising the rare earth oxychloride (MOCl) comprises the following steps: (a) preparing a solution of a chloride salt of the rare earth element or elements in a solvent comprising either water, an alcohol, or mixtures thereof; (b) adding a nitrogen-containing base to cause the formation of a precipitate; and (c) collecting, drying and calcining the precipitate in order to form the MOCl material. Typically, the nitrogen-containing base is selected from ammonium hydroxide, allyl amine, aryl amine, arylalkyl amine, alkyl ammonium hydroxide, aryl ammonium hydroxide, arylalkyl ammonium hydroxide, and mixtures thereof. The nitrogen-containing base may also be provided as a mixture of a nitrogen-containing base with other bases that do not contain nitrogen. Preferably, the nitrogen-containing base is tetra-alkyl ammonium hydroxide. The solvent in Step (a) is preferably water. Drying of the catalytically-useful composition can be done in any manner, including by spray drying, drying in a purged oven and other known methods. For the presently-preferred fluidized bed mode of operation, a spray-dried catalyst is preferred.

A method currently felt to be preferable for forming the catalyst composition comprising the rare earth chloride ($MCl_3$) comprises the following steps: (a) preparing a solution of a chloride salt of the rare earth element or elements in a solvent comprising either water, an alcohol, or mixtures thereof; (b) adding a nitrogen-containing base to cause the formation of a precipitate; (c) collecting, drying and calcining the precipitate; and (d) contacting the calcined precipitate with a chlorine source. For example, one application of this method (using La to illustrate) would be to precipitate $LaCl_3$ solution with a nitrogen containing base, dry it, add it to the reactor, heat it to 400° C. in the reactor to perform the calcination, and then contact the calcined precipitate with a chlorine source to form the catalyst composition in situ in the reactor. Catalysts for preferred use are further clarified by a consideration of examples presented in a subsequent section of this specification.

Ethane/Ethylene To VCM Oxydehydro-chlorination Reactor 202 catalytically reacts together ethane, ethylene, hydrogen chloride, oxygen, and chlorine along with at least one recycle stream to yield Reactor Effluent Stream 232; and it is of special note that the molar ratio of ethane to ethylene derived from all feeds to Ethane/Ethylene To VCM Oxydehydro-chlorination Reactor 202 is between 0.02 and 50 (note that the particular operational ratio at any moment is determined by issues in operational process status) without long-term detriment to catalyst functionality. Depending on market and operational conditions at a particular moment of manufacture, ethylene is added to Reactor 202 via Ethylene Stream 289. In this regard, a more preferred molar ratio of ethane to ethylene derived from all feeds to Ethane/Ethylene To VCM Oxydehydro-chlorination Reactor 202 is between 0.1 and 10. When market and operational conditions (at a particular moment of manufacture) permit, the most preferred mode is for Ethylene Stream 289 to have a flow of zero and for the molar ratio of ethane to ethylene derived from all feeds to Ethane/Ethylene To VCM Oxydehydro-chlorination Reactor 202 to be between 0.3 and 4, with variance therein dependent upon local process conditions and catalyst life-cycle considerations. Even as the Reactor 202 effluent stream (Stream 232) is generated by catalytically reacting together ethane, ethylene, oxygen, and at least one chlorine source of hydrogen chloride, chlorine, or a chlorohydrocarbon, it is to be noted that catalyst selectivity in the conversion of these streams to VCM benefits by, first, conditioning lanthanide-based catalysts with elemental chlorine. Catalyst selectivity in the conversion of these streams to VCM using lanthanide-based catalysts also benefits when elemental chlorine (Steam 228) is included as a portion of the chlorine source to Reactor 202. It should also be noted that any other catalyst systems, which exhibit the capacity to convert both ethane and ethylene to VCM, are advantageously, in alternative embodiments, also used with the VCM process and apparatus herein disclosed.

Chlorine sources (selected from hydrogen chloride, chlorine, and a chlorohydrocarbon) HCl Feed Stream 224, Chlorine Feed Stream 228, any portion of EDC Stream 262 chosen for recycle, and any other recycled or raw material feed streams containing, without limitation, at least one of a chlorinated methane or a chlorinated ethane (for example, without limitation, carbon tetrachloride, 1,2-dichloroethane, ethyl chloride, 1,1-dichloroethane, and 1,1,2-trichloroethane) collectively provide chlorine to the oxydehydro-chlorination reaction; these streams are individually variable from moment to moment in real-time operation for providing the stoichiometric chlorine needed for VCM conversion. With respect to EDC (1,2-dichloroethane) from EDC Stream 262, market conditions affecting the opportunity for direct sale determine the appropriate amount for either recycle to Reactor 202 or direct sale. A further option for use of a portion of EDC Stream 262, dependent upon the particular facility, is for feedstock to a VCM conversion furnace. In this regard, operation of Process 200 is alternatively conducted so that (a) 1,2-dichloroethane generated in Reactor 202 is purified for sale, (b) 1,2-dichloroethane generated in Reactor 202 is purified for recycle to Reactor 202, and/or (c) 1,2-dichloroethane generated Reactor 202 is purified for cracking in a vinyl furnace. It is also to be noted that EDC is also, at occasional times, advantageously purchased for use as a chlorine source.

Ethane/Ethylene To VCM Oxydehydro-chlorination Reactor 202 outputs Reactor Effluent Stream 232 to feed Cooling Condenser 204. Cooling Condenser 204 treats Reactor Effluent Stream 232 to provide (a) a raw product (vapor) stream having a first portion of hydrogen chloride and (b) a raw cooled (aqueous) hydrogen chloride stream having the remainder of the hydrogen chloride which exited Reactor 202; the raw product (vapor) stream is Stream 240.

Stream 234 is conveyed to Phase Separation Subsystem 206 for removal of residual organic compounds from the raw cooled HCl. Phase Separation Subsystem 206 is, in alternative embodiments, a decanter, a stripper, or a combination of a decanter and stripper. From Phase Separation Subsystem 206 the removed organic materials (essentially in liquid phase) are conveyed to Lights Column 210 via Stream 242, and the separated raw cooled (essentially aqueous liquid) HCl is conveyed as Stream 236 to Anhydrous HCl Recovery Subsystem 208. Anhydrous HCl Recovery Subsystem 208 receives (aqueous) Stream 274 from Vent Oxidation Unit (a thermal oxidation or other oxidation unit useful for vent stream purification to acceptable environmental compositions) 214, Stream 278 (aqueous) from Lights HCl Absorption Unit 276, and (aqueous) Stream 236 and generates output stream Stream 266 as anhydrous HCl recycle to Ethane/Ethylene To VCM Oxydehydro-chlorination Reactor 202. Stream 268 outputs water from Anhydrous HCl Recovery Subsystem 208 for subsequent use or to waste recovery. In summary, Anhydrous HCl Recovery Subsystem 208 provides functionality to recover an anhydrous hydrogen chloride stream from the raw cooled hydrogen chloride stream and other aqueous HCl streams of Process 200. Anhydrous HCl Recovery Subsystem 208 also recycles the anhydrous hydrogen chloride (vapor) stream to the reactor. As should be apparent to those of skill, there are other methodologies for separating anhydrous HCl from mixtures of water and HCl.

Cooling Condenser 204 also outputs Stream 240 (vapor) to Lights Column 210 where a lights stream (vapor Stream 244) containing ethylene is further removed from the reactor effluent product stream. Note that, in contrast to the system discussed in FIG. 1, the ethylene from Lights Column 210 is mostly returned as recycle to Ethane/Ethylene To VCM Oxydehydro-chlorination Reactor 202 without conversion to EDC.

After separation of HCl and lights stream (Stream 244) from the reactor effluent, Lights Column 210 forwards Stream 252 for separation of a water product stream, a vinyl chloride monomer product stream (Stream 254), an ethyl chloride stream (Stream 230), a cis-1,2-dichloroethylene and trans-1,2-dichloroethylene blended stream (Stream 260), a 1,2-dichloroethane stream (Stream 262), and a heavies stream (Stream 264). The manner of effecting these final separations is apparent to those of skill, and a substantial number of classically-utilized process units can be deployed in various configurations to achieve these separations. Drying Subsystem 216, VCM Purification Column 218, and Heavies Column 220 conveniently depict, therefore, the general separation systems (and, as such, should have the term "column" interpreted as a "virtual column" representing at least one physical column, although, in one contemplated embodiment, each column could be only a single physical column) for separation of Water Stream 256, VCM Product Stream 254, Ethyl Chloride Stream 230, Cis/trans-1,2-dichloroethylene Stream 260, and EDC Stream 262, with Heavies Stream 264 as organic material for destruction in a waste organic burner or use in an appropriate product where the general properties of Heavies Stream 264 are acceptable. In an alternative contemplated embodiment, Drying Subsystem 216 removes water prior to Lights Column 210, with the effluent from Lights Column 210 being forwarded to VCM Purification Column 218. Note again that, with respect to EDC (1,2-dichloroethane) from EDC Stream 262, market conditions affecting the opportunity for direct sale function to determine the appropriate amount for either recycle to Reactor 202 or direct sale. In this regard, operation of VCM Purification Column 218, and Heavies Column 220 is alternatively conducted so that (a) 1,2-dichloroethane is purified for sale, (b) 1,2-dichloroethane is purified for recycle to Reactor 202, and/or (c) 1,2-dichloroethane is purified for cracking in a vinyl furnace.

Returning now to Stream 244 as it exists from Lights Column 210, Stream 244 is divided into a first stream portion forwarded directly in Stream 248 to Ethane/Ethylene To VCM Oxydehydro-chlorination Reactor 202 and into a second stream which forwards first to Lights HCl Absorption Unit 276 and then to C2 Absorption and Stripping Columns 212. Lights HCl Absorption Unit 276 outputs aqueous HCl as Stream 278 to Anhydrous HCl Recovery Subsystem 208. C2 Absorption and Stripping Columns 212 absorb and strip C2 materials (ethane and ethylene) from the forwarded second stream portion of Stream 244 and insure the recycle of the C2 materials to Reactor 202 via C2 Recycle Stream 246 which, in combination the first stream portion from Stream 244, forms Stream 248. C2 Absorption and Stripping Columns 212 also outputs a purge stream to Vent Oxidation Unit 214 which outputs Vent Stream 250 to the atmosphere and also (aqueous) Stream 274 to Anhydrous HCl Recovery Subsystem 208. CO (carbon monoxide) composition instrumentation provides a measurement (not shown) for use in a control system's (not shown) determination of an appropriate portion of the remaining lights gas for processing via C2 Absorption and Stripping Columns 212 and Vent Oxidation Unit 214 to generate Vent Stream 250 so that CO does not accumulate to unacceptable levels in the process.

Simulated relative stream flows and stream compositions for Ethane to VCM Oxydehydro-chlorination Process 200 are appreciated from a consideration of Table 1. Table 1 (mass unit/time unit) data uses laboratory-derived catalyst performance measurements for lanthanum oxychloride at 400 degrees Celsius and essentially ambient pressure; further details on the preferred catalyst are appreciated from a study of "A PROCESS FOR THE CONVERSION OF ETHYLENE TO VINYL CHLORIDE, AND NOVEL CATALYST COMPOSITIONS USEFUL FOR SUCH PROCESS". Table 1 shows some flows as a zero in the context of the simulation generating the data, but such a numeric value is not intended to mean a total absence of flow or absence of need for a stream Table 1 does not show Ethylene Feed Stream 289; in this regard, and reprising an earlier point, when market and operational conditions at a particular moment of manufacture permit, the most preferred mode is for Ethylene Stream 289 to have a flow of zero. However, under certain conditions, Ethylene Stream 289 does contribute an economically beneficial flow.

TABLE 1

ETHANE/ETHYLENE TO VINYL CHLORIDE MASS BALANCE FOR PROCESS 200

| Stream | $C_2H_6$ | $C_2H_4$ | $O_2$ | HCl | $Cl_2$ | Ar | CO | $CO_2$ | EDC | EtCl | VCM | DCE | $H_2O$ | total |
|---|---|---|---|---|---|---|---|---|---|---|---|---|---|---|
| 222 | 572 | 0 | 0 | 0 | 0 | 0 | 0 | 0 | 0 | 0 | 0 | 0 | 0 | 572 |
| 224 | 0 | 0 | 0 | 0 | 0 | 0 | 0 | 0 | 0 | 0 | 0 | 0 | 0 | 0 |
| 226 | 0 | 0 | 548 | 0 | 0 | 6 | 0 | 0 | 0 | 0 | 0 | 0 | 0 | 553 |
| 228 | 0 | 0 | 0 | 0 | 660 | 0 | 0 | 0 | 0 | 0 | 0 | 0 | 0 | 660 |
| 230 | 0 | 0 | 0 | 0 | 0 | 0 | 0 | 0 | 0 | 22 | 0 | 0 | 0 | 22 |
| 232 | 1847 | 1042 | 19 | 1459 | 0 | 98 | 1257 | 257 | 147 | 22 | 1000 | 127 | 559 | 7834 |
| 234 | 83 | 27 | 0 | 510 | 0 | 0 | 2 | 7 | 142 | 15 | 428 | 116 | 553 | 1883 |
| 236 | 0 | 0 | 0 | 510 | 0 | 0 | 0 | 0 | 0 | 0 | 0 | 0 | 553 | 1063 |
| 240 | 1765 | 1015 | 19 | 949 | 0 | 98 | 1255 | 251 | 5 | 7 | 572 | 11 | 6 | 5951 |
| 242 | 83 | 27 | 0 | 0 | 0 | 0 | 2 | 7 | 142 | 15 | 428 | 116 | 0 | 820 |
| 244 | 1847 | 1042 | 19 | 949 | 0 | 98 | 1257 | 257 | 0 | 0 | 0 | 0 | 0 | 5469 |
| 246 | 99 | 56 | 0 | 0 | 0 | 0 | 0 | 0 | 0 | 0 | 0 | 0 | 0 | 154 |
| 248 | 1842 | 1039 | 18 | 896 | 0 | 93 | 1186 | 243 | 0 | 0 | 0 | 0 | 0 | 5316 |
| 250 | 0 | 0 | 0 | 0 | 0 | 6 | 0 | 150 | 0 | 0 | 0 | 0 | 13 | 168 |
| 252 | 0 | 0 | 0 | 0 | 0 | 0 | 0 | 0 | 147 | 22 | 1000 | 127 | 0 | 1296 |
| 254 | 0 | 0 | 0 | 0 | 0 | 0 | 0 | 0 | 0 | 0 | 1000 | 0 | 0 | 1000 |
| 256 | 0 | 0 | 0 | 0 | 0 | 0 | 0 | 0 | 0 | 0 | 0 | 0 | 6 | 6 |
| 260 | 0 | 0 | 0 | 0 | 0 | 0 | 0 | 0 | 0 | 0 | 0 | 127 | 0 | 127 |
| 262 | 0 | 0 | 0 | 0 | 0 | 0 | 0 | 0 | 147 | 0 | 0 | 0 | 0 | 147 |
| 264 | 0 | 0 | 0 | 0 | 0 | 0 | 0 | 0 | 0 | 0 | 0 | 0 | 0 | 0 |
| 266 | 0 | 0 | 0 | 564 | 0 | 0 | 0 | 0 | 0 | 0 | 0 | 0 | 0 | 564 |
| 268 | 0 | 0 | 0 | 0 | 0 | 0 | 0 | 0 | 0 | 0 | 0 | 0 | 553 | 553 |
| 274 | 0 | 0 | 0 | 0 | 0 | 0 | 0 | 0 | 0 | 0 | 0 | 0 | 0 | 0 |
| 278 | 0 | 0 | 0 | 53 | 0 | 0 | 0 | 0 | 0 | 0 | 0 | 0 | 113 | 167 |

Figure 3:
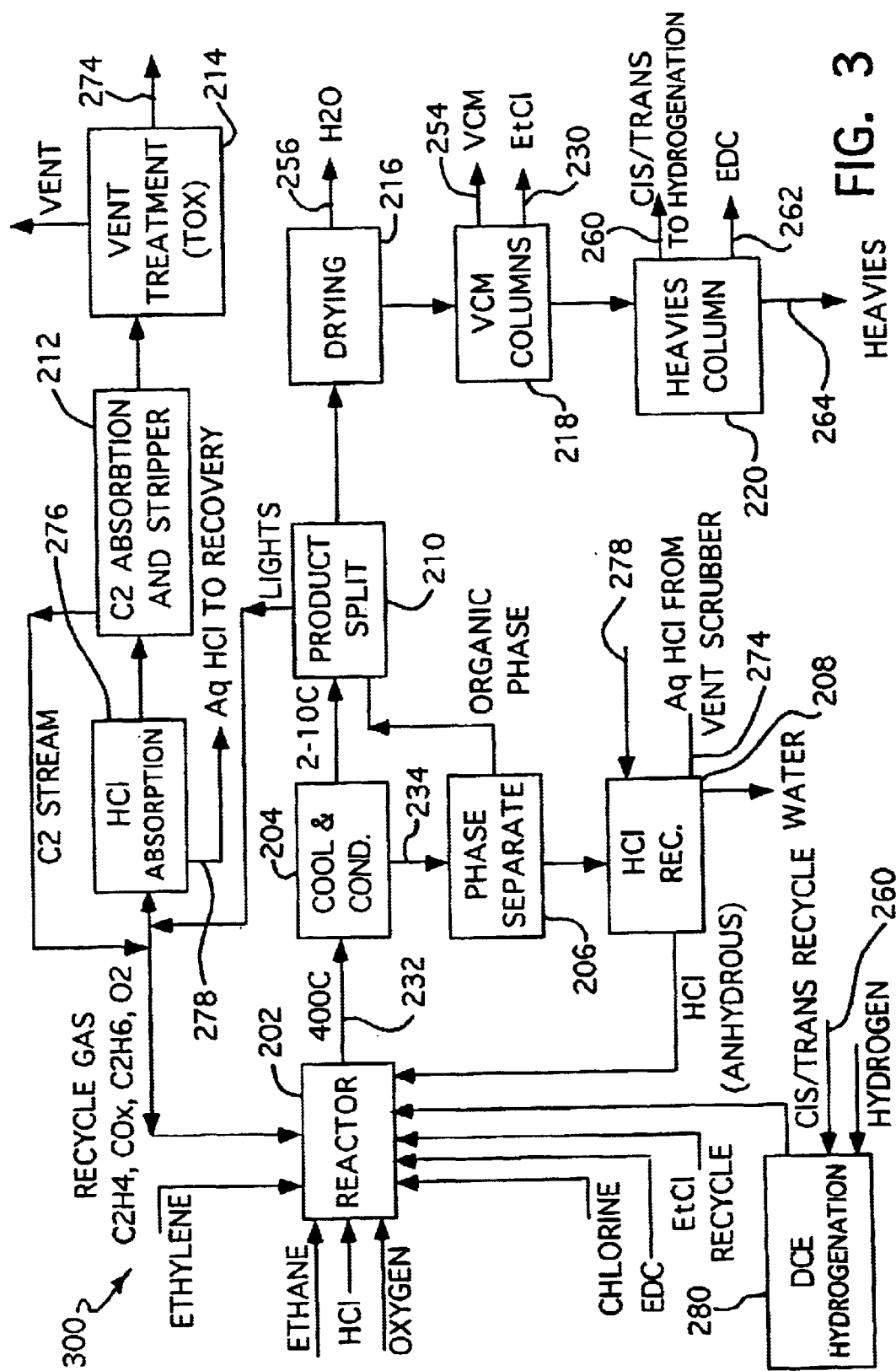
FIG. 3 modifies the oxydehydro-chlorination process of FIG. 2 to show further hydrogenation of cis-dichloroethylene and trans-dichloroethylene streams to 1,2-dichloroethane.

Turning now to FIG. 3, Ethane to VCM Oxydehydro-chlorination With Cis/Trans Recycle Process 300 modifies Ethane to VCM Oxydehydro-chlorination Process 200 with DCE (dichloroethylene) Hydrogenation Unit 280 for (a) hydrogenating cis-1,2-dichloroethylene and trans-1,2-dichloroethylene from Cis/trans-1,2-dichloroethylene Stream 260 and (b) recycling the output stream to Reactor 202. In an alternative embodiment, Streams 230, 260, and 262 are separated as one single blended stream in Heavies Column 220 and the single blended stream is recycled to DCE Hydrogenation Unit 280.

Table 2 presents further detail in components identified in the Figures.

TABLE 2

Component detail

| Drawing Element | Name | Description |
|---|---|---|
| 102 | Reactor | Fluid bed ethane reactor. Vertically oriented reactor system with gas feed at bottom and outlet at top. Vertical cooling tubes in bed and internal cyclones (up to 3 in series) located at the top. Typical diameters up to 20 feet. Height of fluid bed 30 to 50 feet, with total height of 80 feet. The reactor temperature of >400° C. requires that a high nickel alloy be used for construction. |
| 104 | RCL Hydrogenation | Hydrogenation reactor for converting the unsaturated compounds (most are chlorinated, such as cis-1,2 dichloroethylene or trans-1,2 dichloroethylene) to their saturated derivatives for recycle to the reactor. |
| 106 | Cool and Scrub | Product gas from the reactor is cooled and the condensate separated from the vapor. The condensate has both a concentrated HCl aqueous phase and an organic phase. |
| 108 | Phase Separate | Gravity separation of the aqueous and organic phases from Cooler 106 is preferably achieved with a horizontal tank provided with internal baffles to allow the heavy phase (most likely the aqueous/acid phase, but the nature of the phases depend on the exact composition of organics in the phases) to be removed from one end of the vessel. The lighter phase flows over the baffle into the second half of the vessel for removal. The aqueous phase is then, in some embodiments, stripped of organics. |
| 110 | HCl Recovery | The aqueous HCl stream from the separator is recovered as anhydrous HCl for recycle to the reactor using traditionally deployed approaches which are apparent to those of skill. |
| 112 | Direct Chlorination | Reactor for the chlorination of ethylene. This is typically accomplished by injecting the chlorine and ethylene into the bottom of a vessel containing EDC. The reactants form EDC; the net product removed as an overhead vapor. The heat of reaction provides the driving force for the vaporization. |
| 114 | Product Split | Separation column, with refrigerated condensers at the top to allow separation of the lights for recycle from the chlorinated organics. |
| 116 | EDC Recovery | Standard distillation columns for the purification of EDC. |
| 118 | Vent Treatment (TOX) | Vent treatment is achieved with an incinerator for the oxidation of organics (including chlorinated organics) to water vapor, carbon dioxide, and hydrogen chloride. The vent gas is scrubbed with water to recover HCl as a relatively dilute (10 to 20% HCl stream) for other uses. This unit is typical of those found throughout the chemical industry and should be apparent to those of skill. |
| 120 | Drying | Prior to the final separation of the VCM from the other products, water is removed in a drying column. The pressure and temperature are adjusted such that the water is removed from the bottom of the column and the dry product is removed from the top. |
| 122 | VCM Columns | Final purification of the VCM product as practiced in industry. |

TABLE 2-continued

Component detail

| Drawing Element | Name | Description |
|---|---|---|
| 124 | Recycle Products Column | A distillation column to effect the separation of the cis and trans 1,2 dichloroethylenes and EDC from the heavier (higher molecular weight) components. The recovered components are sent to the hydrogenation reactor prior to recycling to the reactor. |
| 202 | Reactor | Ethylene/ethane oxydehydro-chlorination reactor. A fluid bed version (preferred) of the reactor is a vertically oriented reactor system with gas feed at bottom and with the outlet at the top. Vertical cooling tubes are positioned in the bed, and internal cyclones (up to 3 in series) are located at the top. Typical diameter of the reactor is less than 20 feet. Height of fluid bed is between 30 feet and 50 feet, with a total height of 80 feet for the reactor. The fixed bed version of the reactor is a vertical exchanger type catalytic reactor with tubes from 1 to 1.5 inches diameter. The reactor temperature of >400° C. requires that a high nickel alloy be used for construction. |
| 204 | Cool and Condense | Effluent gas from the reactor is cooled with a graphite block or graphite tube heat exchanger. The condensate has both a concentrated HCl aqueous phase and an organic phase. |
| 206 | Phase Separate | Gravity separation of the aqueous and organic phases from Step 204 is preferably achieved with a horizontal tank provided with internal baffles to allow the heavy phase (most likely the aqueous/acid phase, but the nature of the phases depend on the exact composition of organics in the phases) to be removed from one end of the vessel. The lighter phase flows over the baffle into the second half of the vessel for removal. The aqueous phase is then, in some embodiments, stripped of organics. |
| 208 | HCl Recovery | The aqueous HCl stream from the separator is recovered as anhydrous HCl for recycle to the reactor using traditionally deployed approaches which are apparent to those of skill. |
| 210 | Product Split | A separation column, with refrigerated condensers at the top to allow separation of the lights for recycle from the chlorinated organics, is preferably used for this splitting operation. |
| 212 | C2 Absorption and Stripper | Recovery of ethane and ethylene in the purge stream is achieved by absorption into a hydrocarbon or other absorbing liquid in an absorber, with a stripping operation in a second column. The recovered hydrocarbons are then recycled "back" to the main recycle stream and further to the reactor. |
| 214 | Vent Treatment (TOX) | Vent treatment is achieved with an incinerator for the oxidation of organics (including chlorinated organics) to water vapor, carbon dioxide, and hydrogen chloride. The vent gas is scrubbed with water to recover HCl as a relatively dilute (10 to 20% HCl stream) for other uses. This unit is typical of those found throughout the chemical industry and should be apparent to those of skill. |
| 216 | Drying | Prior to the final separation of the VCM from the other products in the raw product stream after lights have been stripped, water is removed in a drying column. The pressure and temperature are preferably adjusted such that the water is removed from the bottom of the column and the dry product is removed from the top. |
| 218 | VCM Columns | VCM is purified by methods as practiced in industry and apparent to those of skill. |
| 220 | Heavies Column | Heavies are separated using a distillation column effecting the separation of (a) the cis and trans 1,2 dichloroethylenes and (b) EDC from heavier (higher molecular weight) components. |
| 276 | HCl Absorption | HCl absorption is achieved with a scrubber column removing HCl from the gas stream into an aqueous solution. |
| 280 | Hydrogenation | Hydrogenation is achieved in a reactor for converting the unsaturated compounds (most being chlorinated, such as cis or trans 1,2 dichloroethylenes) to their saturated derivatives for recycle to the reactor. |

EXAMPLES

Specifics in catalysts are further clarified by a consideration of the following examples, which are intended to be purely exemplary.

Example 1

To demonstrate the production of vinyl chloride from a stream comprising ethylene, a porous, refractory composition comprising lanthanum was prepared. A solution of $LaCl_3$ in water was prepared by dissolving one part of commercially available hydrated lanthanum chloride (obtained from J.T. Baker Chemical Company) in 8 parts of deionized water. Dropwise addition with stirring of ammonium hydroxide (obtained from Fisher Scientific, certified ACS specification) to neutral pH (by universal test paper) caused the formation of a gel. The mixture was centrifuged, and the solution decanted away from the solid. Approximately 150 ml of deionized water was added and the gel was stirred vigorously to disperse the solid. The resulting solution was centrifuged and the solution decanted away. This washing step was repeated two additional times. The collected, washed gel was dried for two hours at 120 degrees Celsius and subsequently calcined at 550 deg. C. for four hours in air. The resulting solid was crushed and sieved to yield particles suitable for additional testing. This procedure produced a solid matching the X-ray powder diffraction pattern of LaOCl.

The particles were placed in a pure nickel (alloy 200) reactor. The reactor was configured such that ethylene, ethane, HCl, $O_2$ and inert gas (He and Ar mixture) could be fed to the reactor. The function of the argon was as an internal standard for the analysis of the reactor feed and effluent by gas chromatography. Space time is calculated as the volume of catalyst divided by the flow rate at standard conditions. Feed rates are molar ratios. The reactor system was immediately fed an ethane-containing stream with the stoichiometry of one ethane, one HCl and one oxygen. This provides balanced stoichiometry for the production of VCM from ethylene.

Table 3 below sets forth the results of reactor testing using this composition.

Column 1 of Table 3 shows the high selectivity to vinyl chloride when the catalyst system is fed ethylene under oxidizing conditions in the presence of HCl. The composition contains helium in order to mimic a reactor operated with air as the oxidant gas.

Column 2 of Table 3 shows the high selectivity to vinyl chloride when the catalyst system is fed ethylene under oxidizing conditions in the presence of HCl. The composition is now fuel rich to avoid limitations imposed by flammability and contains no helium.

Column 3 of Table 3 shows the high selectivity to vinyl chloride and ethylene when the catalyst system is fed ethane under oxidizing conditions in the presence of HCl. The composition mimics a reactor operated with air as the oxidant gas. There is no ethylene present in the feed. The ethylene present in the reactor is the product of the partial oxidation of ethane.

Column 4 of Table 3 shows the result when both ethane and ethylene are fed. The reactor is operated in such a way as to insure that the amount of ethylene entering the reactor and exiting the reactor are equal. Operated in this fashion, the ethylene gives the appearance of an inert diluent, and only ethane is being converted. The results show a high yield of vinyl chloride and 1,2-dichloroethane. Argon is used as an internal standard to insure that the ethylene flux entering the reactor and the ethylene flux exiting the reactor are equal. The ratio of the ethylene to argon integrated chromatographic peak is identical for the reactor feed and product stream. In this way the recycle of ethylene is simulated within the reactor device.

TABLE 3

|  | Feed Mole Ratios | | | |
| --- | --- | --- | --- | --- |
| $C_2H_4$ | 2 | 3.7 | 0 | 3 |
| $C_2H_6$ | 0 | 0 | 1 | 2 |
| HCl | 2 | 2 | 1 | 2.5 |
| $O_2$ | 1 | 1 | 1 | 1 |
| Inerts | 6.8 | 0 | 4 | 0 |
| T (deg. C.) | 401 | 400 | 401 | 419 |
| Space time (s) | 12.3 | 5.0 | 21.8 | 12.4 |
| $O_2$ conv. (pct) | 47.3 | 53.7 | 54.8 | 93.9 |
|  | Selectivities (Percent) | | | |
| $C_2H_4$ | — | — | 44.7 | — |
| $C_2H_4Cl_2$ | 10.7 | 14.0 | 0.1 | 12.8 |
| VCM | 76.6 | 78.1 | 34.5 | 68.5 |

Example 2

To further demonstrate the utility of the composition, ethylene is oxidatively converted to vinyl chloride using a variety of chlorine sources. A solution of $LaCl_3$ in water was prepared by dissolving one part of commercially available hydrated lanthanum chloride (purchased from Avocado Research Chemicals Ltd.) in 6.6 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 550 deg C. for four hours in air. The resulting solid was crushed and sieved. The sieved particles were placed in a pure nickel (alloy 200) reactor. The reactor was configured such that ethylene, HCL, oxygen, 1,2-dichloroethane, carbon tetrachloride and helium could be fed to the reactor. Space time is calculated as the volume of catalyst divided by the flow rate at standard temperature and pressure. Feed rates are molar ratios. The composition was heated to 400 deg C. and treated with a 1:1:3 $HCl:O_2:He$ mixture for 2 hours prior to the start of operation.

The composition formed was operated to produce vinyl chloride by feeding ethylene, a chlorine source and oxygen at 400 deg C. The following table shows data obtained between 82 and 163 hours on stream using different chlorine sources. Chlorine is supplied as HCl, carbon tetrachloride and 1,2-dichloroethane. VCM signifies vinyl chloride. Space time is calculated as the volume of catalyst divided by the flow rate at standard temperature and pressure. The reactors are operated with the reactor exit at ambient pressure. Both ethylene and 1,2-dichloroethane are termed to be $C_2$ species.

TABLE 4

|  | Feed mole ratios | | | |
| --- | --- | --- | --- | --- |
| $C_2H_4$ | 2.0 | 2.0 | 2.0 | 2.0 |
| $C_2H_6$ | 0.0 | 0.0 | 0.0 | 0.0 |
| $CCl_4$ | 0.5 | 0.5 | 0.0 | 0.0 |
| $C_2H_4Cl_2$ | 0.0 | 0.0 | 1.8 | 0.0 |
| HCl | 0.0 | 0.0 | 0.0 | 1.9 |
| $O_2$ | 1.0 | 1.0 | 1.0 | 1.0 |
| He + Ar | 8.9 | 9.0 | 8.9 | 6.7 |
| T (deg C.) | 400 | 399 | 401 | 400 |
| Space time (s) | 8.0 | 4.0 | 8.6 | 4.9 |
|  | Fractional conversions (Percent) | | | |
| $C_2H_4$ | 40.4 | 27.0 | 18.7 | 20.1 |
| $C_2H_6$ | 0.0 | 0.0 | 0.0 | 0.0 |
| $CCl_4$ | 94.8 | 78.4 | 0.0 | 0.0 |
| $C_2H_4Cl_2$ | 0.0 | 0.0 | 98.3 | 0.0 |
| HCl | 0.0 | 0.0 | 0.0 | 44.7 |
| $O_2$ | 68.8 | 42.0 | 55.2 | 37.8 |
|  | Selectivities based on moles of $C_2$ converted | | | |
| VCM | 59.6 | 56.4 | 86.0 | 78.5 |
| $C_2H_4Cl_2$ | 14.8 | 30.7 | 0.0 | 2.2 |
| $C_2H_5Cl$ | 0.6 | 0.4 | 0.2 | 1.6 |

These data show that a variety of chlorine sources can be used in the oxidative production of vinyl. The use of carbon tetrachloride, 1,2-dichloroethane and HCl all produce vinyl chloride as the dominant product.

Example 3

A solution of $LaCl_3$ in water was prepared by dissolving one part of commercially available hydrated lanthanum chloride (purchased from Avocado Research Chemicals Ltd.) in 6.67 parts of deionized water. Rapid addition with stirring of 6 M ammonium hydroxide in water (diluted certified ACS reagent, obtained from Fisher Scientific) caused the formation of a gel and yielded a final pH of 8.85. The mixture was filtered to collect the solid. The collected material was calcined in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor.

Table 5 shows data wherein the reactor feeds were adjusted such that the flux of ethylene (moles/minute) entering the reactor and the flux of ethylene exiting the reactor were substantially equal. Reactor feeds were similarly adjusted such that the fluxes of HCl entering and exiting the reactor were substantially equal. Oxygen conversion was set at slightly less than complete conversion to enable the monitoring of catalyst activity. Operated in this manner, the consumed feeds are ethane, oxygen, and chlorine. Both ethylene and HCl give the appearance of neither being created nor consumed. Space time is calculated as the volume of catalyst divided by the flow rate at standard temperature and pressure. The example further illustrates the use of chlorine gas as a chlorine source in the production of vinyl chloride.

TABLE 5

| | Feed mole ratios |
|---|---|
| $C_2H_4$ | 2.1 |
| $C_2H_6$ | 4.5 |
| $Cl_2$ | 0.5 |
| HCl | 2.4 |
| $O_2$ | 1.0 |
| He + Ar | 7.4 |
| T (° C.) | 400 |
| Space time (s) | 9.4 |
| | Fractional conversions (Pct.) |
| $C_2H_4$ | 1.8 |
| $C_2H_6$ | 27.3 |
| $Cl_2$ | 99.8 |
| HCl | −1.4 |
| $O_2$ | 96.4 |
| | Selectivities (Pct) |
| VCM | 79.0 |
| $C_2H_4Cl_2$ | 7.2 |
| $C_2H_5Cl$ | 1.7 |
| $CO_x$ | 5.1 |
| $C_2H_4$ | 0.5 |

In common with all examples herein, VCM signifies vinyl chloride. $C_2H_4Cl_2$ is solely 1,2-dichloroethane. COX is the combination of CO and $CO_2$.

Example 4 through Example 11

Example 4 through Example 11 illustrate the preparation of numerous rare earth compositions, each containing only one rare earth material. Data illustrating the performance of these compositions are set forth in Table 6.

Example 4

A solution of $LaCl_3$ in water was prepared by dissolving one part of commercially available hydrated lanthanum chloride (purchased from Aldrich Chemical Company) in 6.67 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The gel was resuspended in 6.66 parts of deionized water. Centrifuging allowed collection of the gel. The collected gel was dried at 120 deg C. prior to calcination at 550 deg C. for four hours in air. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. Powder x-ray diffraction shows the material to be LaOCl. The BET surface area is measured to be 42.06 $m^2/g$. The specific performance data for this example are set forth below in Table 6.

Example 5

A solution of $NdCl_3$ in water was prepared by dissolving one part of commercially available hydrated neodymium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. Powder x-ray diffraction shows the material to be NdOCl. The BET surface area is measured to be 22.71 $m^2/g$. The specific performance data for this example are set forth below in Table 6.

Example 6

A solution of $PrCl_3$ in water was prepared by dissolving one part of commercially available hydrated praseodymium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. Powder x-ray diffraction shows the material to be PrOCl. The BET surface area is measured to be 21.37 $m^2/g$. The specific performance data for this example are set forth below in Table 6.

Example 7

A solution of $SmCl_3$ in water was prepared by dissolving one part of commercially available hydrated samarium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCL oxygen, and inert (helium and argon mixture) could be fed to the reactor. Powder x-ray diffraction shows the material to be SmOCl. The BET surface area is measured to be 30.09 $m^2/g$. The specific performance data for this example are set forth below in Table 6.

Example 8

A solution of $HoCl_3$ in water was prepared by dissolving one part of commercially available hydrated holmium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 20.92 $m^2/g$. The specific performance data for this example are set forth below in Table 6.

Example 9

A solution of $ErCl_3$ in water was prepared by dissolving one part of commercially available hydrated erbium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCL oxygen, and inert (helium and argon mixture) could be fed to the reactor. The BET surface area is measured to be 19.80 m$^2$/g. The specific performance data for this example are set forth below in Table 6.

Example 10

A solution of YbCl$_3$ in water was prepared by dissolving one part of commercially available hydrated ytterbium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 2.23 m$^2$/g. The specific performance data for this example are set forth below in Table 6.

Example 11

A solution of YCl$_3$ in water was prepared by dissolving one part of commercially available hydrated yttrium chloride (Alfa Aesar) in 6.67 parts of deionized water. Rapid addition with stirring of 6 M ammonium hydroxide in water (diluted certified ACS reagent, obtained from Fisher Scientific) caused the formation of a gel. The mixture was filtered to collect the solid. The collected gel was dried at 120 deg C. prior to calcination at 500 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 29.72 m$^2$/g. The specific performance data for this example are set forth below in Table 6.

TABLE 6

Rare Earth Oxychloride Compositions Operated to Produce Vinyl Chloride

| Example | 5 | 6 | 7 | 8 | 9 | 10 | 11 | 12 |
|---|---|---|---|---|---|---|---|---|
| Feed mole ratios | | | | | | | | |
| $C_2H_4$ | 3.6 | 4.2 | 3.7 | 3.6 | 3.6 | 3.6 | 4.2 | 3.6 |
| HCl | 2.0 | 2.3 | 2.0 | 2.0 | 2.0 | 2.0 | 2.3 | 2.0 |
| $O_2$ | 1.0 | 1.0 | 1.0 | 1.0 | 1.0 | 1.0 | 1.0 | 1.0 |
| He + Ar | 0.2 | 0.2 | 0.2 | 0.2 | 0.2 | 0.2 | 0.2 | 0.2 |
| T (deg C.) | 399 | 403 | 401 | 400 | 400 | 400 | 400 | 399 |
| Space time (s) | 8.7 | 21.3 | 11.4 | 17.6 | 17.7 | 22.8 | 23.1 | 21.3 |
| Fractional conversions (Percent) | | | | | | | | |
| $C_2H_4$ | 23.7 | 13.2 | 22.8 | 14.7 | 12.7 | 15.4 | 3.3 | 13.8 |
| HCl | 47.6 | 24.9 | 40.9 | 20.8 | 15.9 | 22.4 | 5.0 | 19.8 |
| $O_2$ | 58.8 | 59.4 | 55.0 | 53.4 | 48.1 | 48.8 | 21.2 | 47.8 |
| Selectivities (Percent) | | | | | | | | |
| VCM | 75.3 | 74.4 | 74.2 | 61.0 | 33.3 | 44.0 | 6.1 | 35.0 |
| $C_2H_4Cl_2$ | 11.3 | 2.9 | 6.1 | 2.9 | 14.5 | 17.5 | 8.8 | 18.8 |

TABLE 6-continued

Rare Earth Oxychloride Compositions Operated to Produce Vinyl Chloride

| Example | 5 | 6 | 7 | 8 | 9 | 10 | 11 | 12 |
|---|---|---|---|---|---|---|---|---|
| $C_2H_5Cl$ | 3.5 | 6.9 | 4.4 | 10.6 | 16.8 | 12.8 | 37.0 | 16.5 |
| $CO_x$ | 4.8 | 11.8 | 9.7 | 22.4 | 33.8 | 23.1 | 26.4 | 27.5 |

These data show the utility of bulk rare earth containing compositions for the conversion of ethylene containing streams to vinyl chloride.

Example 12 through Example 16

Example 12 through Example 16 illustrate the preparation of numerous rare earth compositions, each containing a mixture of rare earth materials. Data illustrating the performance of these data are set forth in Table 7.

Example 12

A solution of LaCl$_3$ and NdCl$_3$ in water was prepared by dissolving one part of commercially available hydrated lanthanum chloride (purchased from Spectrum Quality Products) and 0.67 parts of commercially available hydrated neodymium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.96. The mixture was centrifuged to collect the solid. Solution was decanted away from the gel and discarded. The collected gel was dried at 80 deg C. prior to calcination in air at 550 deg. C for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 21.40 m$^2$/g. The specific performance data for this example are set forth below in Table 7.

Example 13

A solution of LaCl$_3$ and SmCl$_3$ in water was prepared by dissolving one part of commercially available hydrated lanthanum chloride (purchased from Spectrum Quality Products) and 0.67 parts of commercially available hydrated samarium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.96. The mixture was centrifuged to collect the solid. Solution was decanted away from the gel and discarded. The collected gel was dried at 80 deg C. prior to calcination in air at 550 deg. C for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 21.01 m$^2$/g. The specific performance data for this example are set forth below in Table 7.

Example 14

A solution of LaCl$_3$ and YCl$_3$ in water was prepared by dissolving one part of commercially available hydrated lanthanum chloride (purchased from Spectrum Quality Products) and 0.52 parts of commercially available hydrated yttrium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.96. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert helium and argon mixture) could be fed to the reactor. The BET surface area is measured to be 20.98 $m^2/g$. The specific performance data for this example are set forth below in Table 7.

Example 15

A solution of $LaCl_3$ and $HoCl_3$ in water was prepared by dissolving one part of commercially available hydrated lanthanum chloride (purchased from Spectrum Quality Products) and one part of commercially available hydrated holmium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 8.64. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 19.68 $m^2/g$. The specific performance data for this example are set forth below in Table 7.

Example 16

A solution of $LaCl_3$ and $HoCl_3$ in water was prepared by dissolving one part of commercially available hydrated lanthanum chloride (purchased from Spectrum Quality Products) and 0.75 parts of commercially available hydrated ytterbium chloride (Alfa Aesar) in 13.33 parts of deionized water. Rapid addition with stirring of 6 M ammonium hydroxide in water (diluted certified ACS reagent, obtained from Fisher Scientific) caused the formation of a gel. The final pH was measured as 9.10. The mixture was centrifuged to collect the solid. Solution was decanted away from the gel and discarded. The collected gel was dried at 80 deg C. prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 20.98 $m^2/g$. The specific performance data for this example are set forth below in Table 7.

TABLE 7

Performance of Compositions Containing Two Rare earth materials

| Example | 13 | 14 | 15 | 16 | 17 |
|---|---|---|---|---|---|
| | Feed mole ratios | | | | |
| $C_2H_4$ | 3.7 | 3.6 | 3.6 | 3.6 | 3.6 |
| HCl | 2.0 | 2.0 | 2.0 | 2.0 | 2.0 |
| $O_2$ | 1.0 | 1.0 | 1.0 | 1.0 | 1.0 |
| He + Ar | 0.2 | 0.2 | 0.2 | 0.2 | 0.2 |
| T (° C.) | 401 | 401 | 400 | 399 | 400 |
| Space time (s) | 3.7 | 15.7 | 13.7 | 16.9 | 20.6 |
| | Fractional conversions (Percent) | | | | |
| $C_2H_4$ | 16.8% | 11.3 | 12.5 | 12.4 | 9.2 |
| HCl | 36.0 | 13.1 | 18.1 | 11.9 | 15.9 |
| $O_2$ | 45.9 | 47.2 | 52.2 | 47.1 | 38.7 |
| | Selectivities (Percent) | | | | |
| VCM | 75.8 | 51.0 | 51.4 | 28.9 | 11.1 |
| $C_2H_4Cl_2$ | 9.7 | 7.5 | 12.4 | 14.5 | 20.6 |
| $C_2H_5Cl$ | 4.1 | 11.8 | 8.9 | 17.0 | 23.8 |
| $CO_x$ | 6.9 | 27.5 | 25.8 | 38.9 | 43.8 |

These data further show the utility of bulk rare earth containing compositions containing mixtures of the rare earth materials for the conversion of ethylene containing streams to vinyl chloride.

Example 17 through Example 24

Example 17 through Example 24 are compositions containing rare earth materials with other additives present.

Example 17

A solution of $LaCl_3$ in water was prepared by dissolving one part of commercially available hydrated lanthanum chloride (purchased from Aldrich Chemical Company) in 6.67 parts of deionized water. 0.48 parts of ammonium hydroxide (Fisher Scientific) was added to 0.35 parts of commercially prepared $CeO_2$ powder (Rhone-Poulenc). The lanthanum and cerium containing mixtures were added together with stirring to form a gel. The resulting gel containing mixture was filtered and the collected solid was calcined in air at 550 deg C. for 4 hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The specific performance data for this example are set forth below in Table 8.

Example 18

A lanthanum containing composition prepared using the method of Example 5 was ground with a mortar and pestle to form a fine powder. One part of the ground powder was combined with 0.43 parts $BaCl_2$ powder and further ground using a mortar and pestle to form an intimate mixture. The lanthanum and barium containing mixture was pressed to form chunks. The chunks were calcined at 800 deg C. in air for 4 hours. The resulting material was placed in a pure nickel (alloy 200) reactor. The reactor was configured such that ethylene, ethane, HCl, oxygen, and inert (helium and argon mixture) could be fed to the reactor. The specific performance data for this example are set forth below in Table 8.

Example 19

Dried Grace Davison Grade 57 silica was dried at 120 deg C. for 2 hours. A saturated solution of $LaCl_3$ in water was formed using commercially available hydrated lanthanum chloride. The dried silica was impregnated to the point of incipient wetness with the $LaCl_3$ solution. The impregnated silica was allowed to air dry for 2 days at ambient temperature. It was further dried at 120 deg C. for 1 hour. The resulting material was placed in a pure nickel (alloy 200) reactor. The reactor was configured such that ethylene, ethane, HCl, oxygen, and inert (helium and argon mixture) could be fed to the reactor. The specific performance data for this example are set forth below in Table 8.

Example 20

A solution of $LaCl_3$ in water was prepared by dissolving one part of commercially available hydrated lanthanum chloride (purchased from Spectrum Quality Products) in 6.67 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The gel was resuspended in 12.5 parts of acetone (Fisher Scientific), centrifuged, and the liquid decanted away and discarded. The acetone washing step was repeated 4 additional times using 8.3 parts acetone. The gel was resuspended in 12.5 parts acetone and 1.15 parts of hexamethyldisilizane (purchased from Aldrich Chemical Company) was added and the solution was stirred for one hour. The mixture was centrifuged to collect the gel. The collected gel was allowed to air dry at ambient temperature prior to calcination in air at 550 deg C. for four hours. The resulting solid was crushed and sieved. The sieved particles were placed in a pure nickel (alloy 200) reactor. The reactor was configured such that ethylene, ethane, HCl, oxygen, and inert (helium and argon mixture) could be fed to the reactor. The BET surface area is measured to be 58.82 $m^2/g$. The specific performance data for this example are set forth below in Table 8.

Example 21

A solution of $LaCl_3$ in water was prepared by dissolving one part of commercially available hydrated lanthanum chloride (Alfa Aesar) and 0.043 parts of commercially available $HfCl_4$ (purchased from Acros Organics) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The collected gel was dried at 80 deg C. overnight prior to calcination at 550 deg C. for 4 hours. The specific performance data for this example are set forth below in Table 8.

Example 22

A solution of $LaCl_3$ in water was prepared by dissolving one part of commercially available hydrated lanthanum chloride (Alfa Aesar) and 0.086 parts of commercially available $HfCl_4$ (purchased from Acros Organics) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded The collected gel was dried at 80 deg C. overnight prior to calcination at 550 deg C. for 4 hours. The specific performance data for this example are set forth below in Table 8.

Example 23

A solution of $LaCl_3$ in water was prepared by dissolving one part of commercially available hydrated lanthanum chloride (Alfa Aesar) and 0.043 parts of commercially available $ZrOCl_2$ (purchased from Acros Organics) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. The gel was resuspended in 6.67 parts deionized water and subsequently centrifuged. The solution was decanted away and discarded. The collected gel was calcined at 550 deg C. for 4 hours. The specific performance data for this example are set forth below in Table 8.

Example 24

A solution of $LaCl_3$ in water was prepared by dissolving commercially available hydrated lanthanum chloride in deionized water to yield a 2.16 M solution. Commercially produced zirconium oxide (obtained from Engelhard) was dried at 350 deg C. overnight. One part of the zirconium oxide was impregnated with 0.4 parts of the $LaCl_3$ solution. The sample was dried in air at room temperature and then calcined in air at 550 deg C. for 4 hours. The resulting solid was crushed and sieved. The sieved particles were placed in a pure nickel (alloy 200) reactor. The reactor was configured such that ethylene, ethane, HCL oxygen, and inert (helium and argon mixture) could be fed to the reactor. The specific performance data for this example are set forth below in Table 8.

TABLE 8

Rare Earth Compositions with Additional Components

| Example | 18 | 19 | 20 | 21 | 22 | 23 | 24 | 25 |
|---|---|---|---|---|---|---|---|---|
| Feed mole ratios | | | | | | | | |
| $C_2H_4$ | 3.7 | 3.6 | 3.7 | 3.7 | 3.7 | 3.7 | 3.6 | 3.7 |
| HCl | 2.0 | 2.0 | 2.0 | 2.0 | 2.0 | 2.0 | 2.0 | 2.0 |
| $O_2$ | 1.0 | 1.0 | 1.0 | 1.0 | 1.0 | 1.0 | 1.0 | 1.0 |
| He + Ar | 0.2 | 0.2 | 0.2 | 0.2 | 0.2 | 0.2 | 0.2 | 0.2 |
| T (° C.) | 400 | 401 | 400 | 399 | 401 | 400 | 400 | 401 |
| Space time (s) | 4.8 | 20.3 | 6.7 | 3.6 | 7.9 | 7.8 | 12.8 | 16.7 |
| Fractional conversions (Percent) | | | | | | | | |
| $C_2H_4$ | 18.2 | 11.7 | 14.1 | 24.6 | 18.5 | 16.5 | 18.7 | 15.2 |
| HCl | 34.6 | 22.1 | 24.4 | 57.1 | 40.9 | 38.2 | 35.2 | 21.1 |
| $O_2$ | 55.6 | 33.2 | 48.0 | 52.0 | 50.3 | 47.4 | 50.9 | 56.4 |
| Selectivities (Percent) | | | | | | | | |
| VCM | 64.5 | 54.6 | 53.6 | 56.0 | 76.4 | 71.8 | 73.2 | 55.1 |
| $C_2H_4Cl_2$ | 11.5 | 15.2 | 10.0 | 31.4 | 9.6 | 12.7 | 5.2 | 7.3 |
| $C_2H_5Cl$ | 5.0 | 10.0 | 7.4 | 2.9 | 4.0 | 4.9 | 4.9 | 12.4 |
| $CO_x$ | 10.8 | 18.6 | 26.6 | 6.0 | 7.6 | 8.8 | 13.6 | 24.1 |

These data show the production of vinyl chloride from ethylene containing streams using lanthanum-based catalysts that contain other elements or are supported.

Example 25 through Example 30

Example 25 through Example 30 show some of the modifications possible to alter the preparation of useful rare earth compositions.

Example 25

A solution of LaCl$_3$ in water was prepared by dissolving one part of commercially available hydrated lanthanum chloride (purchased from Spectrum Quality Products) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. Solution was decanted away from the gel and discarded. A saturated solution of 0.61 parts benzyltriethylammonium chloride (purchased from Aldrich Chemical Company) in deionized water was prepared. The solution was added to the gel and stirred. The collected gel was calcined at 550 deg C. for 4 hours. The specific performance data for this example are set forth below in Table 9. This example illustrates the use of added ammonium salts to alter the preparation of rare earth compositions.

Example 26

A solution of LaCl$_3$ in water was prepared by dissolving one part of commercially available hydrated lanthanum chloride (purchased from Spectrum Quality Products) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. One part glacial acetic acid was added to the gel and the gel redissolved. Addition of the solution to 26 parts of acetone caused the formation of a precipitate. The solution was decanted away and the solid was calcined at 550 deg C. for 4 hours. The specific performance data for this example are set forth below in Table 9. This example shows the preparation of useful lanthanum compositions by the decomposition of carboxylic acid adducts of chlorine containing rare earth compounds.

Example 27

A solution of LaCl$_3$ in water was prepared by dissolving one part of commercially available hydrated lanthanum chloride (purchased from Spectrum Quality Products) in 10 parts of deionized water. Rapid addition with stirring of 6 M ammonium hydroxide in water (diluted certified ACS reagent, obtained from Fisher Scientific) caused the formation of a gel. The mixture was centrifuged to collect the solid. The collected gel was resuspended in 3.33 parts of deionized water. Subsequent addition of 0.0311 parts of phosphoric acid reagent (purchased from Fisher Scientific) produced no visible change in the suspended gel. The mixture was again centrifuged and the solution decanted away from the phosphorus containing gel. The collected gel was calcined for at 550 deg C. for 4 hours. The calcined solid had a BET surface area of 33.05 m$^2$/g. The specific performance data for this example are set forth below in Table 9. This example shows the preparation of a rare earth composition also containing phosphorus, as phosphate.

Example 28

A solution of LaCl$_3$ in water was prepared by dissolving one part of commercially available hydrated lanthanum chloride (purchased from Acros Organics) in 6.66 parts of deionized water. A solution was formed by mixing 0.95 parts of commercially available DABCO, or 1,4-diazabicyclo[2.2.2]octane, (purchased from ICN Pharmaceuticals) dissolved in 2.6 parts of deionized water. Rapid mixing with stirring of the two solutions caused the formation of a gel. The mixture was centrifuged to collect the solid. The collected gel was resuspended in 6.67 parts of deionized water. The mixture was again centrifuged and the solution decanted away from the gel. The collected gel was calcined for 4 hours at 550 deg C. The calcined solid had a BET surface area of 38.77 m$^2$/g. The specific performance data for this example are set forth below in Table 9. This example shows the utility of an alkyl amine in the preparation of a useful rare earth composition.

Example 29

A solution of LaCl$_3$ in water was prepared by dissolving one part of commercially available hydrated lanthanum chloride (purchased from Acros Organics) in 10 parts of deionized water. To this solution, 2.9 parts of commercially available tetramethyl ammonium hydroxide (purchased from Aldrich Chemical Company) was added rapidly and with stirring, causing the formation of a gel. The mixture was centrifuged and the solution decanted away. The collected gel was resuspended in 6.67 parts of deionized water. The mixture was again centrifuged and the solution decanted away from the gel. The collected gel was calcined for 4 hours at 550 deg C. The calcined solid had a BET surface area of 80.35 m$^2$/g. The specific performance data for this example are set forth below in Table 9. This example shows the utility of an alkyl ammonium hydroxide for formation of a useful rare earth composition.

Example 30

A solution of LaCl$_3$ in water was prepared by dissolving one part of commercially available hydrated lanthanum chloride (purchased from Avocado Research Chemicals Ltd.) in 6.67 parts of deionized water. To this solution, 1.63 parts of commercially available 5 N NaOH solution (Fisher Scientific) was added rapidly and with stirring, causing the formation of a gel. The mixture was centrifuged and the solution decanted away. The collected gel was calcined for 4 hours at 550 deg C. The calcined solid had a BET surface area of 16.23 m$^2$/g. The specific performance data for this example are set forth below in Table 9. This example shows the utility of non-nitrogen containing bases for the formation of catalytically interesting materials. Although potentially functional the tested materials appear to be inferior to those produced using nitrogen containing bases.

TABLE 9

Additional Preparation Methods for Lanthanum Containing Compositions

| Example | 26 | 27 | 28 | 29 | 30 | 31 |
|---|---|---|---|---|---|---|
| Feed mole ratios | | | | | | |
| $C_2H_4$ | 3.6 | 3.7 | 3.6 | 3.7 | 3.7 | 3.7 |
| HCl | 2.0 | 2.0 | 2.0 | 2.0 | 2.0 | 2.0 |
| $O_2$ | 1.0 | 1.0 | 1.0 | 1.0 | 1.0 | 1.0 |
| He + Ar | 0.2 | 0.2 | 0.2 | 0.2 | 0.2 | 0.2 |
| T (° C.) | 401 | 400 | 400 | 399 | 400 | 401 |
| Space time (s) | 8.6 | 20.8 | 4.7 | 8.7 | 6.2 | 20.0 |
| Fractional conversions (Percent) | | | | | | |
| $C_2H_4$ | 18.8 | 8.7 | 15.6 | 17.4 | 21.0 | 9.3 |
| HCl | 35.8 | 7.7 | 20.0 | 41.5 | 48.4 | 22.3 |
| $O_2$ | 53.0 | 32.6 | 48.8 | 50.6 | 56.8 | 17.9 |
| Selectivities (Percent) | | | | | | |
| VCM | 73.4 | 26.0 | 72.1 | 76.8 | 77.6 | 17.5 |
| $C_2H_4Cl_2$ | 8.7 | 11.9 | 7.1 | 7.3 | 7.8 | 46.2 |

TABLE 9-continued

Additional Preparation Methods for
Lanthanum Containing Compositions

| Example | 26 | 27 | 28 | 29 | 30 | 31 |
|---------|-----|------|------|-----|-----|------|
| $C_2H_5Cl$ | 3.5 | 22.7 | 5.6 | 4.2 | 2.9 | 25.6 |
| $CO_x$ | 9.8 | 38.6 | 12.7 | 7.6 | 6.3 | 9.1 |

The present invention has been described in an illustrative manner. In this regard, it is evident that those skilled in the art, once given the benefit of the foregoing disclosure, may now make modifications to the specific embodiments described herein without departing from the spirit of the present invention. Such modifications are to be considered within the scope of the present invention which is limited solely by the scope and spirit of the appended claims.

We claim:

1. A method of manufacturing vinyl chloride, comprising the steps of:
   generating a reactor effluent stream by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
   cooling and condensing said reactor-effluent stream to provide a raw product stream having a first portion of said hydrogen chloride and a raw cooled hydrogen chloride stream having a second portion of said hydrogen chloride;
   separating said raw product stream into a vinyl chloride monomer product stream and into a lights stream having said first portion of said hydrogen chloride; and
   recycling said lights stream to catalytically react together with said ethane, said ethylene, said oxygen, and said chlorine source in said generating step.

2. The method of claim 1 wherein said catalytically reacting step uses a catalyst comprising a rare earth material component, with the proviso that the catalyst is substantially free of iron and copper and with the further proviso that when the rare earth material component is cerium the catalyst further comprises at least one more rare earth material component other than cerium.

3. The method of claim 2 wherein the rare earth material component is selected from lanthanum, neodymium, praseodymium, and mixtures thereof.

4. The method of claim 3 wherein the rare earth material component is lanthanum.

5. The method of claim 1 wherein said molar ratio is between 0.1 and 10.

6. The method of claim 1 wherein said molar ratio is between 0.3 and 4.

7. The method of claim 1 wherein one said chlorine source is selected from at least one of a chlorinated methane and a chlorinated ethane.

8. The method of claim 1 wherein one said chlorine source is selected from at least one of the chlorinated organic compounds consisting of carbon tetrachloride, 1,2-dichloroethane, ethyl chloride, 1,1-dichloroethane, and 1,1,2-trichloroethane.

9. The method of claim 1 wherein 1,2-dichloroethane generated in said reacting step is purified for sale.

10. The method of claim 1 wherein 1,2-dichloroethane generated in said reacting step is purified for recycle to said reactor.

11. The method of claim 1 wherein 1,2-dichloroethane generated in said reacting step is purified for cracking in a vinyl furnace.

12. A method of manufacturing vinyl chloride, comprising the steps of:
   generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
   cooling and condensing said reactor effluent stream to provide a raw product stream having a first portion of said hydrogen chloride and a raw cooled hydrogen chloride stream having a second portion of said hydrogen chloride;
   separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;
   recovering an anhydrous hydrogen chloride stream from said raw cooled hydrogen chloride stream;
   recycling said anhydrous hydrogen chloride stream to said reactor as said hydrogen chloride reactant; and
   recycling said lights stream to said reactor.

13. The method of claim 12 wherein said catalytically reacting step uses a catalyst comprising a rare earth material component, with the proviso that the catalyst is substantially free of iron and copper and with the further proviso that when the rare earth material component is cerium the catalyst further comprises at least one more rare earth material component other than cerium.

14. The method of claim 13 wherein the rare earth material component is selected from lanthanum, neodymium, praseodymium, and mixtures thereof.

15. The method of claim 14 wherein the rare earth material component is lanthanum.

16. The method of claim 12 wherein said molar ratio is between 0.1 and 10.

17. The method of claim 12 wherein said molar ratio is between 0.3 and 4.

18. The method of claim 12 wherein one said chlorine source is selected from at least one of a chlorinated methane and a chlorinated ethane.

19. The method of claim 12 wherein one said chlorine source is selected from at least one of the chlorinated organic compounds consisting of carbon tetrachloride, 1,2-dichloroethane, ethyl chloride, 1,1-dichloroethane, and 1,1,2-trichloroethane.

20. The method of claim 12 wherein 1,2-dichloroethane generated in said reacting step is purified for sale.

21. The method of claim 12 wherein 1,2-dichloroethane generated in said reacting step is purified for recycle to said reactor.

22. The method of claim 12 wherein 1,2-dichloroethane generated in said reacting step is purified for cracking in a vinyl furnace.

23. A method of manufacturing vinyl chloride, comprising the steps of:
   generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;
   cooling and condensing said reactor effluent stream to provide a raw product stream having a first portion of said hydrogen chloride and a raw cooled hydrogen chloride stream having a second portion of said hydrogen chloride;

separating said raw product stream into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a fights stream having said first portion of said hydrogen chloride;

recovering an anhydrous hydrogen chloride stream from said raw cooled hydrogen chloride stream;

recycling said anhydrous hydrogen chloride stream to said reactor as said hydrogen chloride reactant;

dividing said lights stream into a purge stream and a recycle gas stream;

absorbing hydrogen chloride from said purge stream to separate an aqueous hydrogen chloride stream;

combining said aqueous hydrogen chloride stream with said raw cooled hydrogen chloride stream;

absorbing and recycling to said reactor a C2 stream from said purge stream; and recycling said recycle gas stream to said reactor.

24. The method of claim 23 wherein said catalytically reacting step uses a catalyst comprising a rare earth material component, with the proviso that the catalyst is substantially free of iron and copper and with the further proviso that when the rare earth material component is cerium the catalyst further comprises at least one more rare earth material component other than cerium.

25. The method of claim 24 wherein the rare earth material component is selected from lanthanum, neodymium, praseodymium, and mixtures thereof.

26. The method of claim 25 wherein the rare earth material component is lanthanum.

27. The method of claim 23 wherein said molar ratio is between 0.1 and 10.

28. The method of claim 23 wherein said molar ratio is between 0.3 and 4.

29. The method of claim 23 wherein one said chlorine source is selected from at least one of a chlorinated methane and a chlorinated ethane.

30. The method of claim 23 wherein one said chlorine source is selected from at least one of the chlorinated organic compounds consisting of carbon tetrachloride, 1,2-dichloroethane, ethyl chloride, 1,1-dichloroethane, and 1,1,2-trichloroethane.

31. The method of claim 23 wherein 1,2-dichloroethane generated in said reacting step is purified for sale.

32. The method of claim 23 wherein 1,2-dichloroethane generated in said reacting step is purified for recycle to said reactor.

33. The method of claim 23 wherein 1,2-dichloroethane generated in said reacting step is purified for cracking in a vinyl furnace.

34. A method of manufacturing vinyl chloride, comprising the steps of:

generating a reactor effluent stream from a reactor by catalytically reacting together ethane, ethylene, oxygen, and at least one chlorine source of hydrogen chloride, chlorine, or a chlorohydrocarbon, wherein the molar ratio of said ethane to said ethylene is between 0.02 and 50;

cooling and condensing said reactor effluent stream to provide a raw product stream having a first portion of said hydrogen chloride and a raw cooled hydrogen chloride stream having a second portion of said hydrogen chloride;

separating said raw product steam into a water product stream, a vinyl chloride monomer product stream, an ethyl chloride stream, a cis-1,2-dichloroethylene and trans-1,2-dichloroethylene blended stream, a 1,2-dichloroethane stream, a heavies stream, and a lights stream having said first portion of said hydrogen chloride;

recovering an anhydrous hydrogen chloride stream from said raw cooled hydrogen chloride stream;

recycling said anhydrous hydrogen chloride stream to said reactor as said hydrogen chloride reactant;

dividing said lights stream into a purge stream and a recycle gas stream;

absorbing hydrogen chloride from said purge stream to separate an aqueous hydrogen chloride stream;

combining said aqueous hydrogen chloride stream with said raw cooled hydrogen chloride stream;

hydrogenating said cis-1,2-dichloroethylene and trans-1,2-dichloroethylene blended stream to provide recycle feed to said reactor;

absorbing and recycling to said reactor a C2 stream from said purge stream; and recycling said recycle gas stream to said reactor.

35. The method of claim 34 wherein said catalytically reacting step uses a catalyst comprising a rare earth material component, with the proviso that the catalyst is substantially free of iron and copper and with the further proviso that when the rare earth material component is cerium the catalyst further comprises at least one more rare earth material component other than cerium.

36. The method of claim 35 wherein the rare earth material component is selected from lanthanum, neodymium, praseodymium, and mixtures thereof.

37. The method of claim 36 wherein the rare earth material component is lanthanum.

38. The method of claim 34 wherein said molar ratio is between 0.1 and 10.

39. The method of claim 34 wherein said molar ratio is between 0.3 and 4.

40. The method of claim 34 wherein one said chlorine source is selected from at least one of a chlorinated methane and a chlorinated ethane.

41. The method of claim 34 wherein one said chlorine source is selected from at least one of the chlorinated organic compounds consisting of carbon tetrachloride, 1,2-dichloroethane, ethyl chloride, 1,1-dichloroethane, and 1,1,2-trichloroethane.

42. The method of claim 34 wherein 1,2-dichloroethane generated in said reacting step is purified for sale.

43. The method of claim 34 wherein 1,2-dichloroethane generated in said reacting step is purified for recycle to said reactor.

44. The method of claim 34 wherein 1,2-dichloroethane generated in said reacting step is purified for cracking in a vinyl furnace.

* * * * *

UNITED STATES PATENT AND TRADEMARK OFFICE
CERTIFICATE OF CORRECTION

PATENT NO. : 6,933,417 B1 Page 1 of 1
APPLICATION NO. : 10/130102
DATED : February 17, 2004
INVENTOR(S) : Alexander Huang It is certified that error appears in the above-identified patent and that said Letters Patent is hereby corrected as shown below:

Title page,
Item [*] Notice, delete "by 213 days" and insert -- by 333 days --.

Signed and Sealed this

Twenty-seventh Day of June, 2006

JON W. DUDAS
*Director of the United States Patent and Trademark Office*